United States Patent
Clune

(10) Patent No.: US 6,827,893 B2
(45) Date of Patent: Dec. 7, 2004

(54) FOLDED FASTENER PRODUCTS

(75) Inventor: William Clune, Concord, NH (US)

(73) Assignee: Velcro Industries B.V. (AN)

( * ) Notice: Subject to any disclaimer, the term of this patent is extended or adjusted under 35 U.S.C. 154(b) by 0 days.

(21) Appl. No.: 09/808,645

(22) Filed: Mar. 14, 2001

(65) Prior Publication Data

US 2002/0023321 A1 Feb. 28, 2002

Related U.S. Application Data

(60) Provisional application No. 60/242,877, filed on Oct. 24, 2000, provisional application No. 60/189,240, filed on Mar. 14, 2000, and provisional application No. 60/189,231, filed on Mar. 14, 2000.

(51) Int. Cl.[7] .............................................. B29C 59/04
(52) U.S. Cl. ...................... 264/129; 24/442; 264/167; 264/171.13; 264/172.11; 264/172.14; 264/173.17; 264/173.19
(58) Field of Search ................................ 156/200, 201, 156/204, 227, 462, 242; 264/285, 286, 167, 219, 225, 129, 132, 171.13; 24/442, 300, 452, 301, 450; 604/389–391; 427/171–176, 209, 211; 267/172.11, 172.14, 173.17, 173.19

(56) References Cited

U.S. PATENT DOCUMENTS

| | | | |
|---|---|---|---|
| 3,353,663 A | 11/1967 | Kayser et al. | |
| 3,566,556 A | 3/1971 | Nichols | 52/71 |
| 4,033,348 A | 7/1977 | Cepuritis | 128/287 |
| 4,397,905 A | 8/1983 | Dettmer et al. | 428/180 |
| 4,608,047 A | 8/1986 | Mattingly | 604/387 |

(List continued on next page.)

FOREIGN PATENT DOCUMENTS

| | | |
|---|---|---|
| EP | 0 321 232 B1 | 12/1988 |
| EP | 0 321 234 A1 | 12/1988 |
| EP | 0 324 578 A1 | 10/1989 |
| EP | 0 374 730 B1 | 12/1989 |
| EP | 0 548 050 B1 | 12/1989 |
| EP | 0 491 347 B1 | 12/1991 |
| EP | 0 704 197 A2 | 12/1991 |
| EP | 0 826 354 A2 | 8/1997 |
| EP | 0 795 307 A2 | 9/1997 |
| EP | 826354 | 4/1998 |
| FR | 2750319 | 2/1998 |
| WO | WO 94/23610 | 10/1994 |
| WO | WO 95/05140 | 2/1995 |
| WO | WO 97/31605 | 9/1997 |
| WO | WO99/17631 | 4/1999 |

Primary Examiner—James R. Brittain
(74) Attorney, Agent, or Firm—Fish & Richardson P.C.

(57) ABSTRACT

Fastener products having a multiplicity of fastener elements extending from a strip-form base, the base including first and second attachment members for attachment of a substrate therebetween, are formed by continuously introducing molten resin to a gap defined adjacent a peripheral surface of a rotating mold roll. The resin forms part of the strip-form base of the product at the peripheral mold roll surface and fills an array of fixed cavities defined in the rotating mold roll to form portions of the fastener elements as projections extending from a first side of the sheet-form base. While the resin is on the mold roll, a sheet material is introduced. The sheet material is folded about a longitudinal fold line to form first and second overlapping fold portions and is introduced under conditions selected to cause the second fold portion to become permanently bonded to resin of the base, while leaving the first fold portion remaining free to be subsequently unfolded from said second fold portion about said fold line. The resin is solidified and stripped from the peripheral surface of the mold roll by pulling the projections from their respective cavities. In some embodiments, a spring section is integrally molded with and extends laterally from a fastening section of the fastener product. The spring section is formed by at least one undulation of the sheet form base that allows the spring section to stretch elastically in a lateral direction upon application of lateral tension to the fastening assembly.

37 Claims, 23 Drawing Sheets

U.S. PATENT DOCUMENTS

| | | | |
|---|---|---|---|
| 4,794,028 A | 12/1988 | Fischer | 428/100 |
| 4,846,815 A | 7/1989 | Scripps | 604/391 |
| 4,869,724 A | 9/1989 | Scripps | 604/389 |
| 4,872,243 A | 10/1989 | Fischer | 24/442 |
| 4,894,060 A | 1/1990 | Nestegard | 604/391 |
| 4,946,527 A | 8/1990 | Battrell | 156/60 |
| 5,019,073 A | 5/1991 | Roessler et al. | 604/391 |
| 5,053,028 A | 10/1991 | Zoia et al. | 604/385.1 |
| 5,108,384 A | 4/1992 | Goulait | 604/390 |
| 5,176,670 A | 1/1993 | Roessler et al. | 604/391 |
| 5,176,671 A | 1/1993 | Roessler et al. | 604/391 |
| 5,242,436 A | 9/1993 | Weil et al. | 604/385.2 |
| 5,318,555 A | 6/1994 | Siebers et al. | 604/390 |
| 5,344,416 A | 9/1994 | Niihara | 604/385 |
| 5,354,400 A | 10/1994 | Lavash et al. | 156/227 |
| 5,383,872 A | 1/1995 | Roessler et al. | 604/391 |
| 5,389,094 A | 2/1995 | Lavash et al. | 604/385 |
| 5,403,302 A | 4/1995 | Roessler et al. | 604/391 |
| 5,449,340 A | 9/1995 | Tollini | 602/58 |
| 5,510,161 A | 4/1996 | Lloyd | 428/40 |
| 5,531,732 A | 7/1996 | Wood | 604/391 |
| 5,554,145 A * | 9/1996 | Roe et al. | 604/358 |
| 5,607,635 A | 3/1997 | Melbye et al. | 264/169 |
| 5,620,430 A | 4/1997 | Bamber | 604/385 |
| 5,624,429 A | 4/1997 | Long et al. | 604/391 |
| 5,656,111 A | 8/1997 | Dilnik et al. | 156/66 |
| 5,660,666 A | 8/1997 | Dilnik et al. | 156/259 |
| 5,672,404 A | 9/1997 | Callahan, Jr. et al. | 428/100 |
| 5,676,652 A | 10/1997 | Hunter et al. | 604/391 |
| 5,679,302 A | 10/1997 | Miller et al. | 264/167 |
| 5,691,026 A | 11/1997 | Zinke et al. | 428/100 |
| 5,691,027 A | 11/1997 | Eckhardt et al. | 428/100 |
| 5,759,317 A | 6/1998 | Justmann | 156/66 |
| 5,786,062 A | 7/1998 | Callahan, Jr. et al. | 428/100 |
| 5,845,375 A | 12/1998 | Miller et al. | 24/452 |
| 5,857,245 A | 1/1999 | Sakakibara et al. | 24/452 |
| 5,876,531 A | 3/1999 | Jacobs et al. | 156/66 |
| 5,902,427 A | 5/1999 | Zinke et al. | 156/73.1 |
| 6,221,483 B1 * | 4/2001 | Hilston et al. | 428/343 |

* cited by examiner

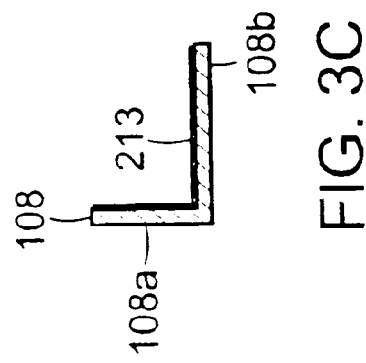
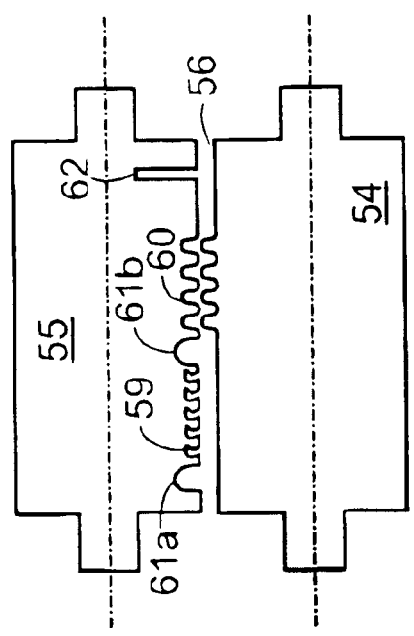
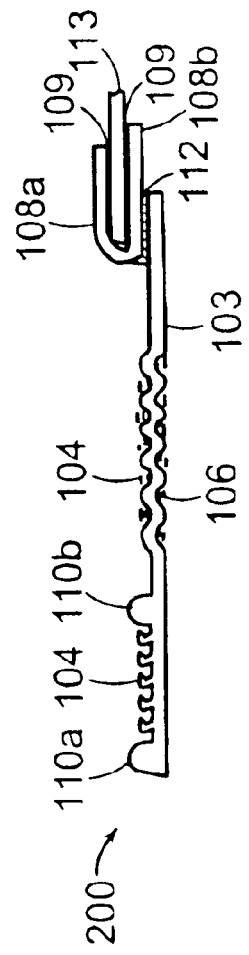

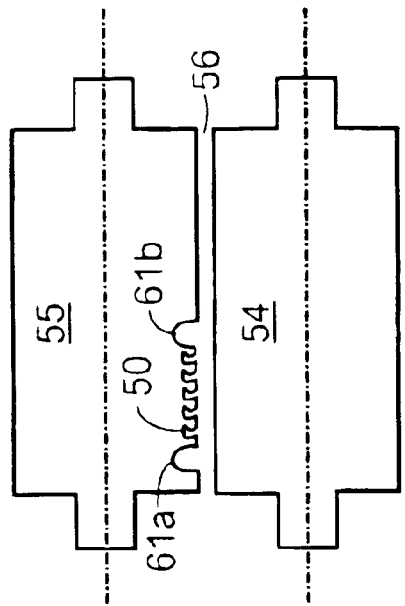
FIG. 4B
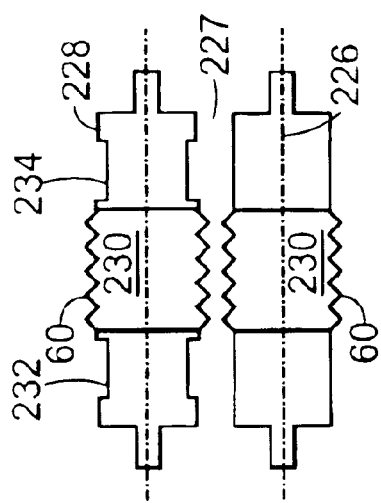
FIG. 4E
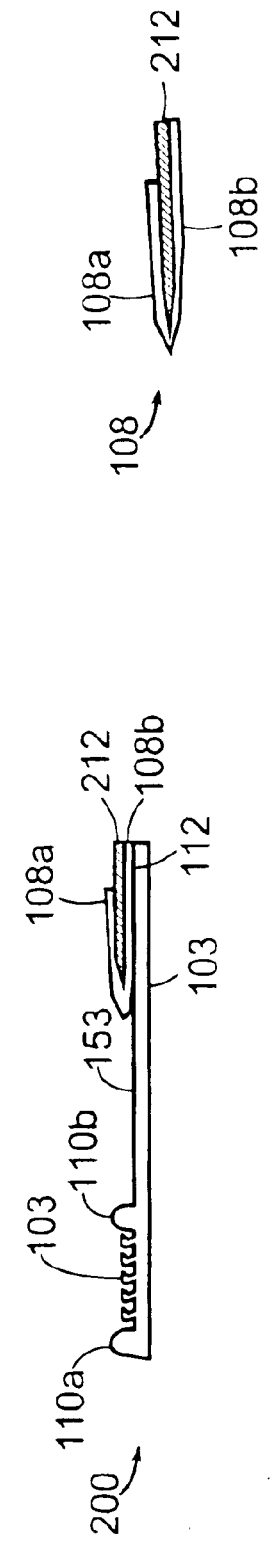
FIG. 4C
FIG. 4D

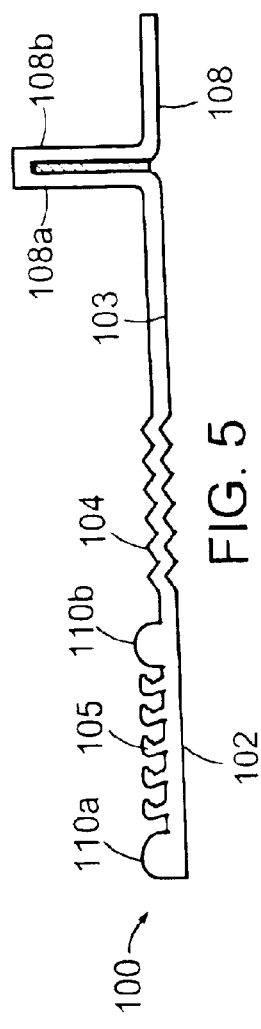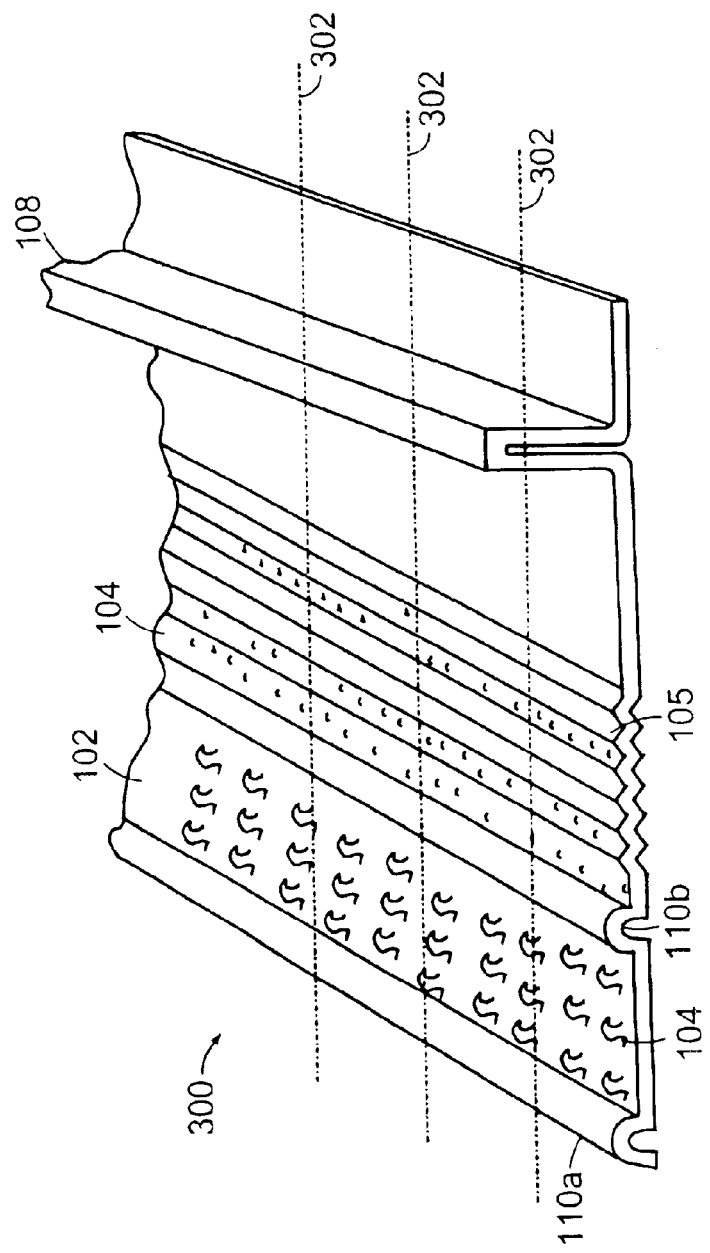

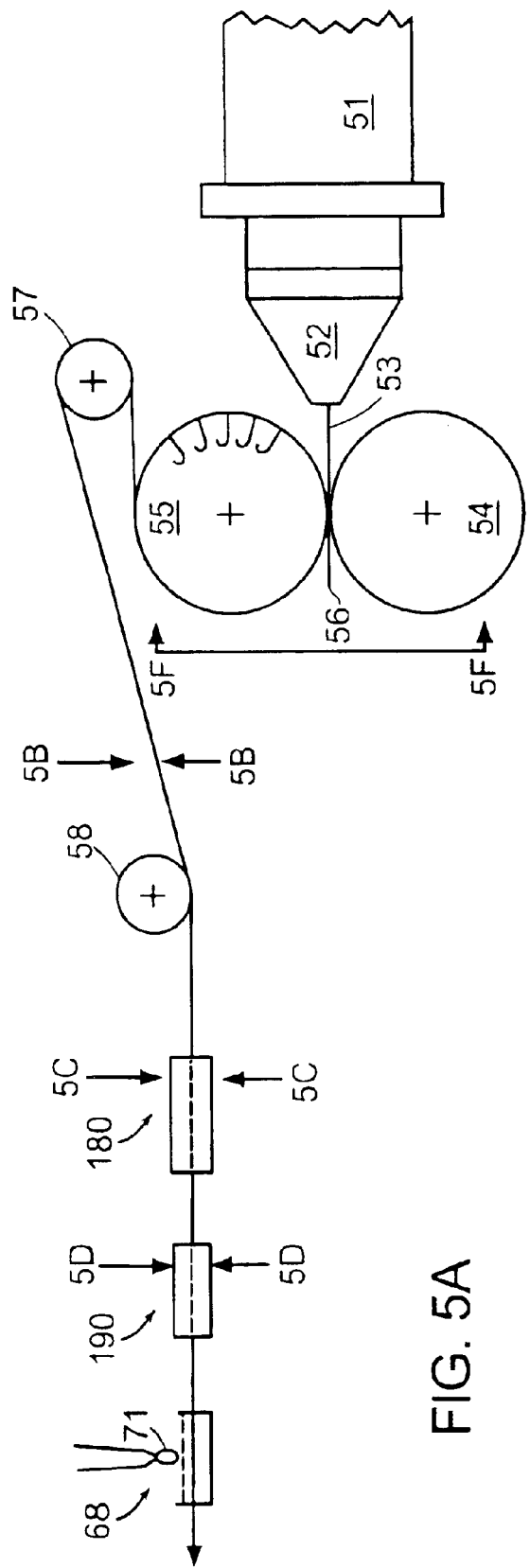
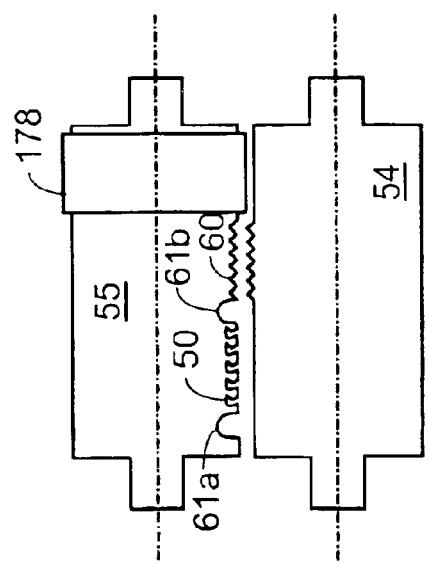
FIG. 5A
FIG. 5F

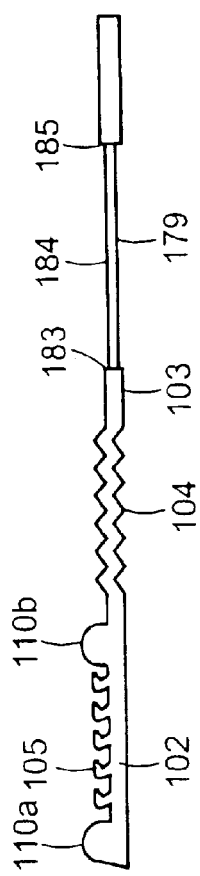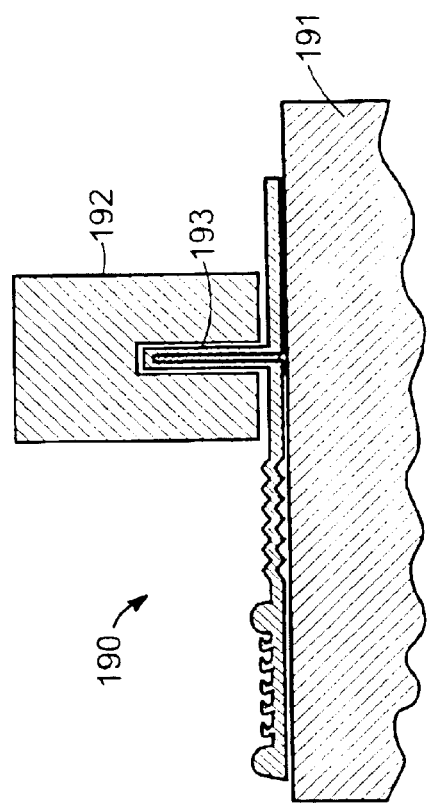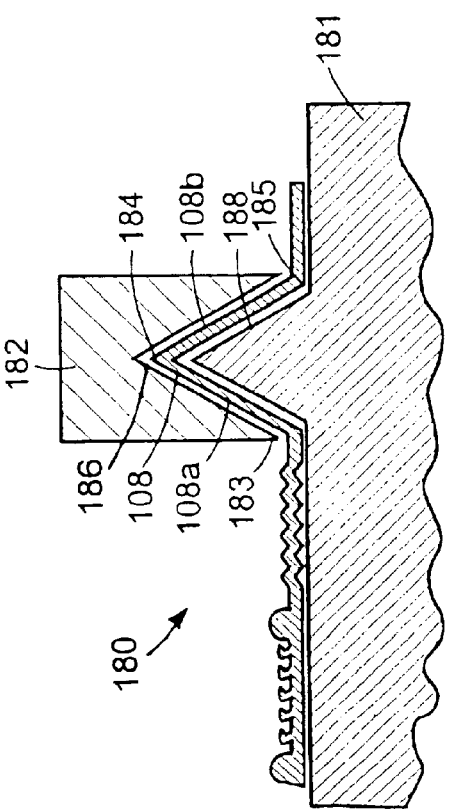
FIG. 5B
FIG. 5D
FIG. 5C

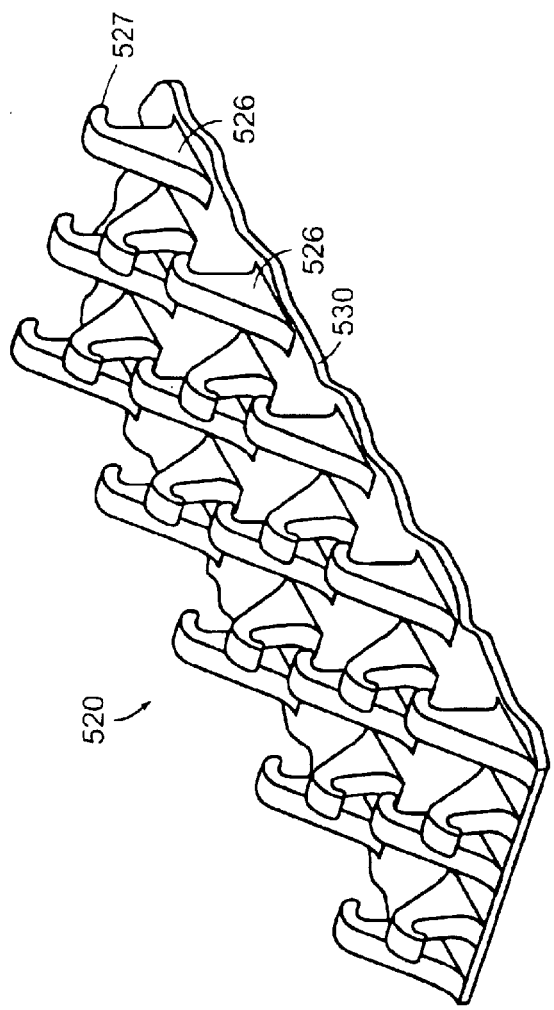
FIG. 10
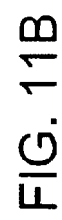
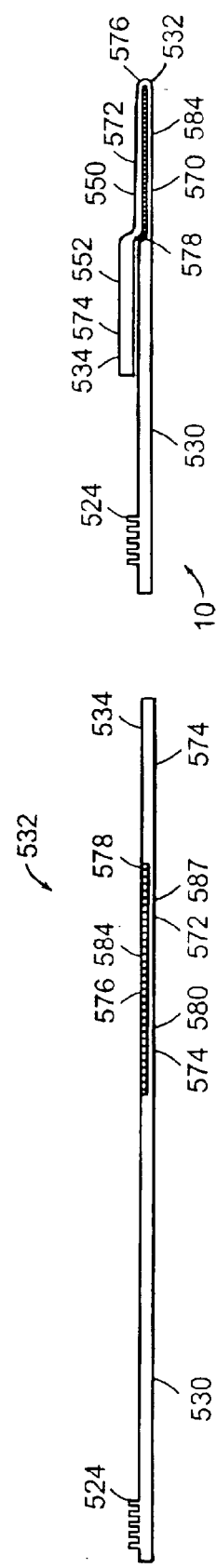
FIG. 11A
FIG. 11B

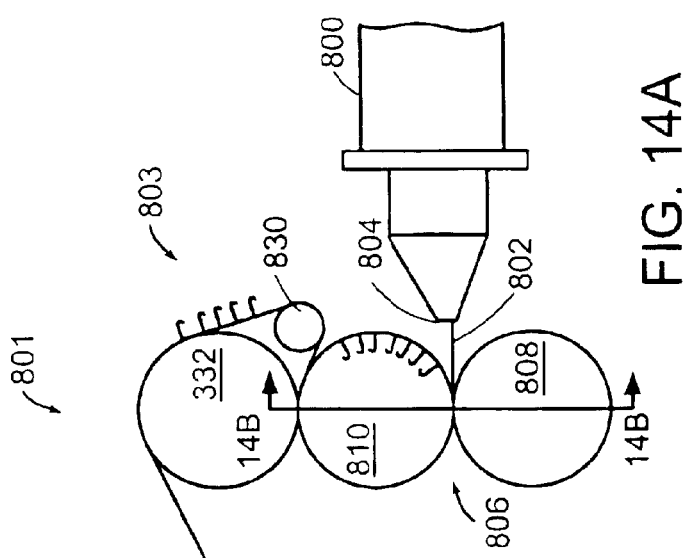
FIG. 14A
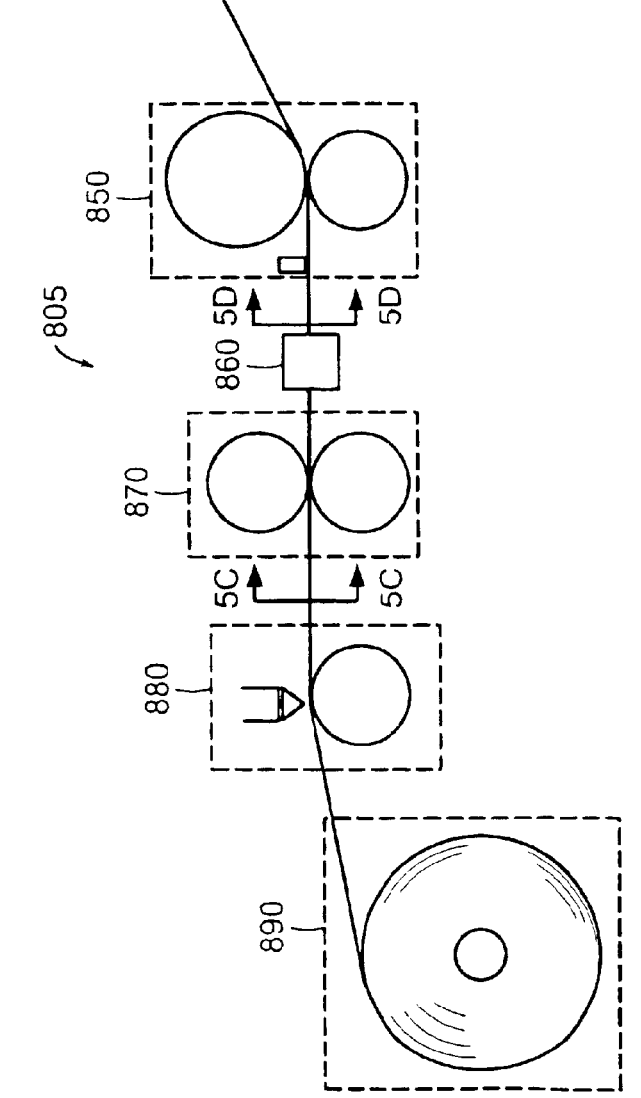
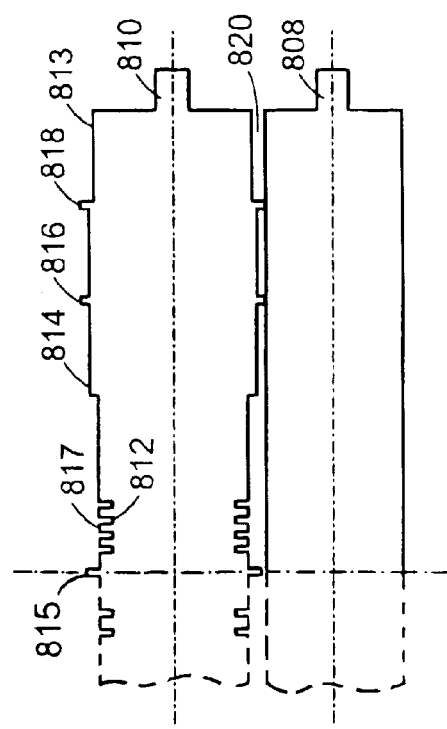
FIG. 14B

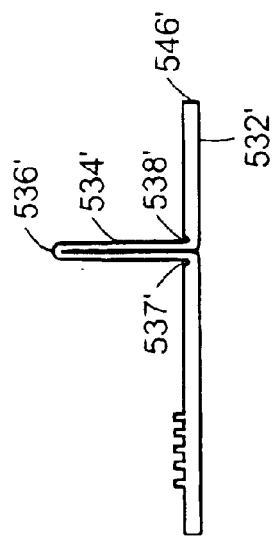
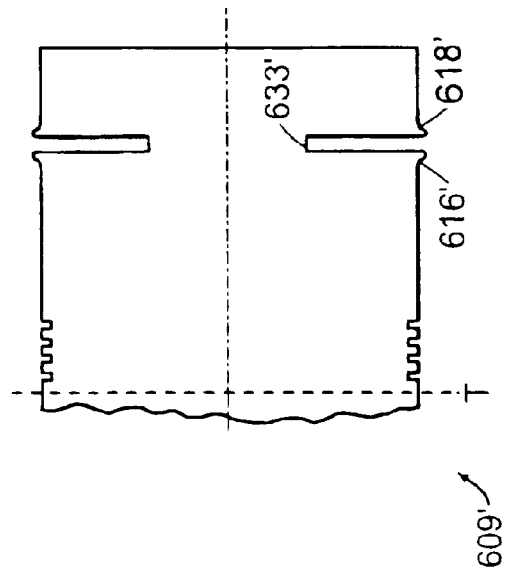

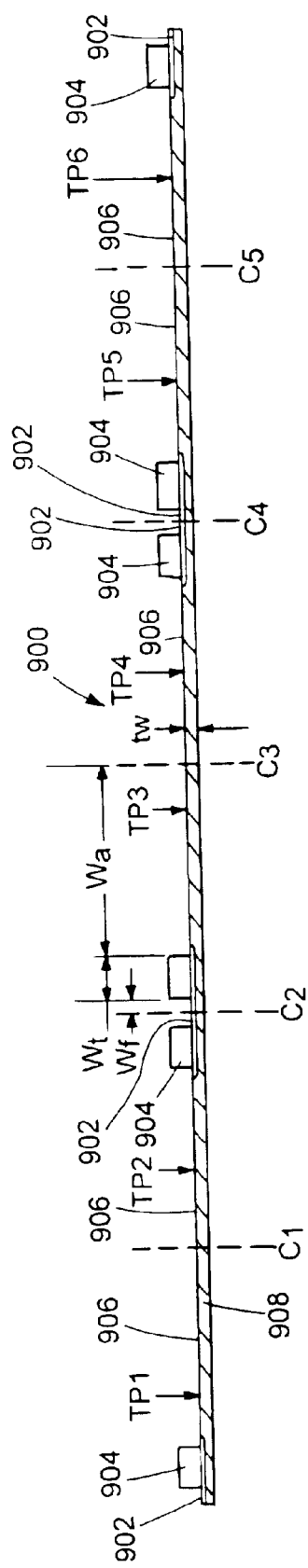
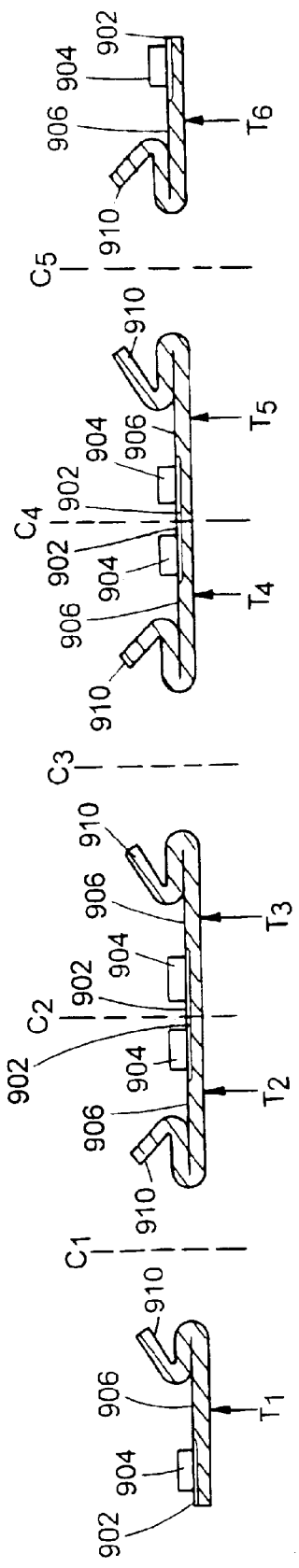
FIG. 22A
FIG. 22B

FOLDED FASTENER PRODUCTS

This application claims the benefit of priority under 35 USC 119 from the following U.S. Provisional Applications: Ser. No. 60/189,231, filed Mar. 14, 2000; Ser. No. 60/189,240, filed Mar. 14, 2000; and Ser. No. 60/242,877 filed Oct. 24, 2000.

BACKGROUND OF THE INVENTION

This invention relates to folded fastening assemblies and method and apparatus for producing and applying the fastening assemblies.

Fastening assemblies that carry hooks or loops are desirable as part of infant and adult diapers, surgical gowns, and other garments and wraps. Fastening assemblies typically comprise a flexible sheet-form film or non-woven web, that has a tab for connecting to an object and a tape of fastener hook elements secured to a surface of the web, forming a laminate structure. The tab of the fastening assembly is attached to one side of an object and the fastener tape is free to engage a hook-engageable surface formed on an opposite side of the object. The fastener tape is typically made of a synthetic resin that is not stretchable, and the resulting laminate is relatively stiff, does not stretch, and does not present the desired degree of cloth-like feel.

Fastening assemblies are often formed by laminating the sheet form film or web with a fastener tape and forming a tab for connecting to an object. One typical application for such fastener tabs is for diaper closure systems. The diaper is generally sold with one end of the fastener tab pre-attached to one of the sides of the diaper and the other end of the fastener tab releasably attachable to the other side of the diaper for securing the diaper around a baby.

It is desirable to provide an economical method of forming fastening assemblies that have a tab and a fastener tape. It is also desirable to provide such assemblies having integral components that achieve desired qualities, such as elasticity, flexibility and low cost and ability to be employed in existing automated assembly systems, such as systems for mass-produced diapers.

SUMMARY OF THE INVENTION

According to one aspect of the invention, a method of forming a fastening product is provided. The fastener product has a multiplicity of fastener elements extending from a strip-form base, the base including first and second attachment members for attachment of a substrate therebetween. The method includes continuously introducing molten resin to a gap defined adjacent a peripheral surface of a rotating mold roll, such that the resin forms part of the strip-form base of the product at the peripheral mold roll surface and fills an array of fixed cavities defined in the rotating mold roll to form portions of the fastener elements as projections extending from a first side of the sheet-form base. The method also includes introducing to the resin on the mold roll a sheet material folded about a longitudinal fold line to form first and second overlapping fold portions, the sheet material introduced under conditions selected to cause the second fold portion to become permanently bonded to resin of the base, while leaving the first fold portion free to be subsequently unfolded from the second fold portion about the fold line. The resin is solidified and stripped from the peripheral surface of the mold roll by pulling the projections from their respective cavities.

Variations of this aspect of the invention can include one or more of the following features. The folded material is folded about multiple fold lines separating more than two fold members. The second fold portion is bonded to the first side of the base from which the fastener elements extend. The second fold portion is bonded to a second side of the base opposite the first side from which the fastener elements extend.

In another aspect of the invention a method of forming a fastening assembly includes molding a continuous sheet-form base having a multiplicity of fastener elements integrally molded with and extending from a fastening section of a surface of the base lying generally in a plane. The base, as molded, has a non-planar undulation in which the base extends out of its plane to form a peak that extends along a longitudinal direction of the base with opposite major surfaces of the base remaining generally parallel. The undulation is elastically deformable to enable the base to stretch laterally upon application of a lateral tensile force to the fastener product.

Variations of this aspect of the invention can include one or more of the following features. The base, as molded, has multiple, parallel undulations, each undulation forming a peak. The undulations are disposed in a region adjacent the fastener elements. The undulations are molded integrally with the fastener section. The undulation is formed by a mating groove and channel of a pair of rolls defining a nip in which the base is formed. The undulation is pre-formed on a material that is introduced into a base-forming nip formed by a pair of rolls; the rolls having a mating groove and channel that accommodate the undulation.

Other variations can include coating the undulation with an elastomer and/or filling an area between adjacent peaks with an elastomer. The elastomer is selected from the group consisting of thermoplastic elastomers, thermoplastic polyurethanes, elastomeric copolymers containing polyethylene terephthalate PET, thermoplastic olefins, and natural or synthetic rubber. The fastener section is molded of resin selected from the group consisting of polyester, polyethylene, polypropylene, polyamide and copolymers and alloys thereof. The method includes forming a tab joined with the base, the tab extending laterally from the undulation along a lateral margin of the fastener assembly opposite a second lateral margin more nearly adjacent the fastening section, the tab comprising at least one flap for joining the fastener assembly to an article. The flap is formed of a section of the base molded integrally with and of the same resin as the portion having the undulation and the fastening section. The flap is formed by folding and permanently joining a portion of the base to another portion of the base. The portion of the base that is folded is thinner than other portions of the base. The Tab is formed by introducing a sheet material into a nip in which the base is molded, the sheet material being folded about a longitudinal fold line to form first and second overlapping fold portions and introduced under conditions selected to cause the second fold portion to become permanently bonded to resin of the base, while leaving the first fold portion free to be subsequently unfolded from the second fold portion about the fold line. The sheet material is bonded to a surface of the base opposite the first surface from which the fastener elements extend. The sheet material is bonded to the first surface of the base from which the fastener elements extend. The second fold portion is bonded to the base only along a margin area of an exposed surface of the second fold portion. Unbonded surface areas of the first and second fold portions are protected from contact with the resin by a protective tape forming a barrier to the resin. Unbonded surface areas of the first and second fold portions are protected from contact with the resin by a protective coating forming a barrier to the resin. The method includes forming dams along edges of the fastening section. The dams are higher than the fastener elements. The step of permanently joining is achieved by heat staking, adhesive or rf-welding together the portion of the base to another portion of the base.

In another aspect of the invention, a method of forming fastener tabs, each tab including a multiplicity of fastener elements extending from a strip-form base and first and second attachment legs for attaching the tab to a garment or substrate therebetween, is disclosed. The method includes continuously introducing molten resin to a gap defined adjacent a peripheral surface of a rotating mold roll, such that the resin forms at least a part of the strip-form base of the product at the peripheral mold roll surface and fills an array of fixed cavities defined in the rotating mold roll to form portions of the fastener elements as projections extending from a first side of the sheet-form base; while introducing a pre-formed material to the resin under conditions selected to cause a portion of the resin to become permanently bonded to the pre-formed material, the preformed material forming at least a part of the strip-form base of the product. The resin is solidified and stripped from the peripheral surface of the mold roll by pulling the projections from their respective cavities. The method further includes folding a portion of the strip-form base to form the first and second attachment legs.

This aspect of the invention can include any of the variation mentioned herein with respect to other aspects of the invention.

In another aspect, the invention is a method of forming fastener tabs, each tab including a multiplicity of fastener elements extending from a strip-form base and first and second attachment legs for attaching the tab to a garment or substrate therebetween. The method includes continuously introducing molten resin to a gap defined adjacent a peripheral surface of a rotating mold roll, such that the resin forms at least a part of the strip-form base of the product at the peripheral mold roll surface and fills an array of cavities defined in the rotating mold roll to form portions of the fastener elements as projections extending from a first side of the sheet-form base. The resin is solidified and stripped from the peripheral surface of the mold roll by pulling the projections from their respective cavities. The method further includes folding a portion of the strip-form base to form the first and second attachment legs.

Variations of this aspect of the invention can include any of the variations mentioned herein with respect to other aspects of the invention.

In another aspect of the invention, a fastening assembly is provided. The fastening assembly includes a multiplicity of fastener elements integrally molded with and extending from a first surface of a sheet-form base to form a fastening section of the fastening assembly, and a spring section integrally molded with and extending laterally from the fastening section, the spring section formed by at least one undulation of the sheet form base that allows the spring section to stretch elastically in a lateral direction upon application of lateral tension to the fastening assembly.

Variations of this aspect of the invention can include one or more of the following features. The undulation is coated with an elastomeric resin. The undulation is triangular. The undulation is sinusoidal. The fastening assembly further includes a tab section having a first and a second attachment leg.

In another aspect, the invention provides a fastener tab including a continuous, unitary strip of thermoplastic resin having first and second end regions, a multiplicity of fastener elements, each having a stem integrally molded with and extending from a surface of the unitary strip disposed in the first end region, and the second end region having two opposable leg portions formed integrally with and of the same material as the continuous strip, the two opposable leg portions positioned to be secured to oppositely directed faces of a substrate or article to support the tab in a manner that the first end may be free to enable its fastener elements to engage a mating surface.

Variations of this aspect of the invention can include one or more of the following features. The leg portions extend from a common hinge region. The strip of thermoplastic resin has a longitudinal profile configured to define at least one hinge region. The hinge region is defined by a localized reduction in thickness of the strip of thermoplastic resin. Portions of the strip of thermoplastic resin are folded together and permanently joined to define the two leg portions. The continuous strip of thermoplastic resin has at least two spaced apart-localized lines of reduced thickness extending longitudinally across the strip to define two hinge regions about which adjacent portions of the strip are folded to constitute the leg portions. The strip, as initially formed, has a substantially longitudinal straight profile with a first hinge region spaced from its adjacent end a first distance and a second hinge region spaced from the end a substantially greater distance, the strip having been bent back upon itself about the second hinge, the bent back portion being permanently joined to the remainder of the strip adjacent to the first hinge region, the outer portion of the strip being free to bend about the first hinge to form an attachment jaw for receiving therebetween a substrate or article to which the oppositely directed surfaces of the respective leg portions may be joined. The bent back portion is permanently joined to the remainder of the strip by adhesive. The bent back portion is permanently joined to the remainder of the strip by ultrasonic bonding. The bent back portion is permanently joined to the remainder of the strip by heat staking.

In another aspect the invention provides a fastener tab. The fastener tab includes a strip form, unitary body consisting essentially of a contiguous resin, the body having a first end and a second end, hooks in a first end region, and two opposable legs in a second end region spaced apart from the hooks for mounting the fastener tab to opposite sides of a substrate.

Variations of this aspect of the invention can include one or more of the following features. The second end region includes a first portion, a second portion, and a hinge therebetween. The second end region is folded about the hinge to overlap the first portion and the second portion. The fastener tab further includes at least one of an adhesive, an ultrasonic weld or a heat stake, joining the overlapped first and second portions. The hinge is defined by a section of decreased thickness. The second region further includes a third portion and a second hinge between the second portion and the third portion. The first portion extends generally in a plane defined by the first end region, and the second portion is folded back over the first portion. The first portion extends out of a plane defined by the first end region, and the second portion is folded back over the first portion. One of the two opposable legs comprises an integrally molded portion extending out of a plane defined by the first end region. The second end region includes a first portion extending generally in a plane defined by the first end region, a second portion folded back over the first portion, and a third portion folded back over the second portion. The second portion forms a first of the two opposable legs, and the third portion forms a second of the two opposable legs. The first and second portions are permanently joined by one of adhesive, heat staking, and ultrasonic welding. The body defines a hinge located between the first portion and the second portion. The body defines a hinge located between the second portion and the third portion. The second end region includes a first portion extending out of a plane defined by the first end region, a second portion folded back over the first portion, and a third portion extending generally in the plane defined by the first end region. The third portion forms a first of the two opposed legs, and the second portion forms a second of the two opposed legs. The first and second portions are permanently joined by one of adhesive, heat staking, and ultrasonic welding. Each of the two opposed legs has an inner facing surface including an adhesive. The adhesive includes a pressure sensitive adhesive. The body is formed of a thermoplastic synthetic resin. The resin includes polypropylene.

In another aspect, the invention provides a roll of fastener tabs joined side-to-side. Each fastener tab includes a strip form, unitary body consisting essentially of a contiguous resin, the body having a first end and a second end, hooks in a first end region, and two opposable legs in a second end region spaced apart from the hooks for mounting the fastener tab to opposite sides of a substrate.

Variations of this aspect of the invention can include one or more of the following features. The two opposable legs are stored in a flat, open position. Each of the two opposed legs has an inner facing surface including an adhesive. The strip form unitary body further includes a release liner covering the adhesive. The body of each tab has projections extending from a surface opposite the adhesive and arranged to be engaged by the adhesive of an overlapping layer of the roll, to limit inter-tab adhesion. The body of each tab has a silicone coating on a surface opposite the adhesive and arranged to be engaged by the adhesive of an overlapping layer of the roll, to limit inter-tab adhesion.

Other features and advantages of the invention will be apparent from the following description of embodiments, and from the claims.

BRIEF DESCRIPTION OF THE DRAWINGS

FIG. 3B is a view of the molding apparatus of FIG. 3A along line 3B—3B.

FIG. 3C is a diagrammatic side view of the non-woven web 108 along lines 3C—3C of FIG. 3A.

FIG. 3D is a diagrammatic cross-sectional side view of the web 200 along lines 3D—3D of FIG. 3A.

FIG. 4B is a view of the molding apparatus of FIG. 4A along line 4B—4B.

FIG. 4C is a diagrammatic side view of the non-woven web 108 along lines 4C—4C in FIG. 4A.

FIG. 4D is a diagrammatic cross-sectional side view of the web 200 along lines 4D—4D in FIG. 4A.

FIG. 4E is a view of the post forming apparatus of FIG. 4A along line 4E—4E.

FIG. 5 is a side, cross-sectional view of another fastening assembly.

FIG. 5A is a side view of an apparatus forming the web of FIG. 5E.

FIG. 5B is a view of the molding apparatus of FIG. 4A along line 4B—4B.

FIG. 5C is a diagrammatic cross-sectional side view of the post processing apparatus 180 along lines 5C—5C in FIG. 5A.

FIG. 5D is a diagrammatic cross-sectional side view of the post processing apparatus 190 along lines 5D—5D in FIG. 5A.

FIG. 5E is a perspective view of a continuous web 300 from which the fastening assembly of FIG. 5 is cut.

FIG. 5F is a view of the molding apparatus of FIG. 5A along line 5F—5F.

FIG. 10 is a highly magnified view of a hook portion of the fastener tab of FIG. 9A.

FIG. 11A is a side view of the fastener tab of FIG. 9A shown in an unfolded state.

FIG. 11B is a side view of the fastener tab of FIG. 9A shown in a partially folded state.

FIG. 14A is a side view of an apparatus for forming a continuous web of fastener tab material.

FIG. 14B is a front view of a molding/calendaring assembly of the apparatus of FIG. 14A, taken along line 14B—14B.

FIG. 17A is a side view of an alternative embodiment of a fastener tab shown in an unfolded state.

FIG. 17B is a side view of the fastener tab of FIG. 17A shown in a folded state.

FIG. 18 is a side view of an alternative embodiment of a fastener tab.

FIG. 19 shows a mold roll for forming the fastener tab of FIG. 18.

FIG. 22A is a cross-sectional view of a tape product of side-by-side fastener tab pre-forms.

FIG. 22B is a cross-sectional view of the fastener tab pre-forms of FIG. 21A folded to form multiple individual fastener tab products.

DESCRIPTION OF EMBODIMENTS

Figure 1A:
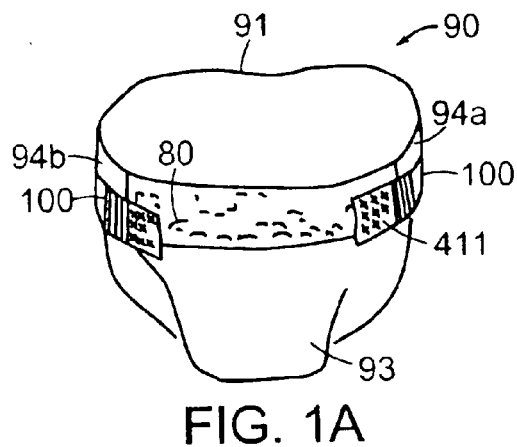
FIG. 1A is a perspective view of a diaper comprising fastening assemblies.

Referring to FIG. 1A two fastening assemblies 100 attach the back side 91 of a diaper 90 to the front side 93 securing the diaper about a body.

Each fastening assembly 100, shown in FIGS. 1B and 1C, features a fastener tape section 102, a stretchy undulating section 104 and a tab section 108, which, in major part, are formed in a single operation as described below. The fastener tape section 102 includes a base 103 and hook-shaped fastening elements 105 integrally molded with and extending from one surface of base 103. The surface of the fastener tape opposite the hooks has embossing or other surface patterns for grasping by the user. Optionally, as shown in the embodiment illustrated in FIGS. 1B–1C, on the hook side of the fastener tape at the left and right edges of the fastener tape section 102 there are two raised dams 110a, 110b, in this case molded integrally with base 103. Dams 110a, 110b are slightly higher than the hook-shaped fastening elements, serving to shield the hooks from accidentally touching and potentially scratching the skin of a baby or other user. The fastening assembly has a width w of the order of ½ inch (1.3 cm) and a length 1 of the order of 4 inches (10.2 cm). The fastener tape section 102 is of width w and has length $1_1$ of the order of 1 inch (2.5 cm). In one example the hooks are of CFM-29 designation, available from Velcro USA Inc. of Manchester, N.H., U.S.A. The CFM-29 hook strip has hooks of only 0.015 inch (0.38 mm) height, a base thickness t 1 of 0.003 inch (0.08 mm) and a fastener element density of the order of 1000 or more fastener elements per square inch. The height of the dams 110a, 110b in this embodiment is about 0.020 inch (0.51 mm).

Other fastener element shapes capable of releasable engagement are also feasible. For example, fastener elements having a mushroom or flat-topped stem shape, a palm-tree shape or any other shape for engaging a loop material are contemplated. Furthermore, fastener elements having shapes capable of releasably engaging other fastener elements of like shape are contemplated as well.

Stretchy section 104 extends from base 103 of the fastener tape section 102 and comprises undulations 107 formed integrally with the base. Elastomeric resin 106 fills the spaces between the undulations 107 and covers them (FIG. 1D). The stretchy section 104 has a length $1_2$ of the order of 1 inch (2.5 cm) and is elastically extensible along the longitudinal direction 120 (FIG. 1B). The stretchy section 104 can be extended or compressed, as shown in FIGS. 1F and 1E, respectively, by at least 50% and, preferably, by at least 100%. In certain embodiments, the undulations are triangular shaped (FIG. 1D), in others, sinusoidal (FIG. 3D). In one example, the undulations have a height $h_u$ of about 0.020 inch (0.51 mm) and a width $w_u$ of about 0.025 inch (0.64 mm) in a relaxed state.

Adjacent to the stretchy undulating section 104 is a tab section 108, formed in part of a base 103a of resin that is integral with the undulations 107 and the fastener section 102. In the embodiment of FIGS. 1B and 1C, the tab 108 further comprises a folded web that has one arm 108b in situ laminated to base 103a and an opposed second arm 108a. The inside surfaces of the tab arms 108a and 108b are coated with an adhesive 109 and the adhesive 109 is covered with a liner 113 which prevents the two arms from adhering to each other. To attach the fastening assembly to the diaper 90 the liner 113 is removed, the side 94 of the diaper is inserted between the two arms 108a, 108b of the tab and laminating pressure is applied.

The front side 93 of the diaper 90 has a hook-engageable band 80 for engaging the fastener elements 105 of the fastener tape 102, thus attaching the back side 91 of the diaper to the front side 93 and securing the diaper to the body of a baby (FIG. 1A).

Figure 1B:
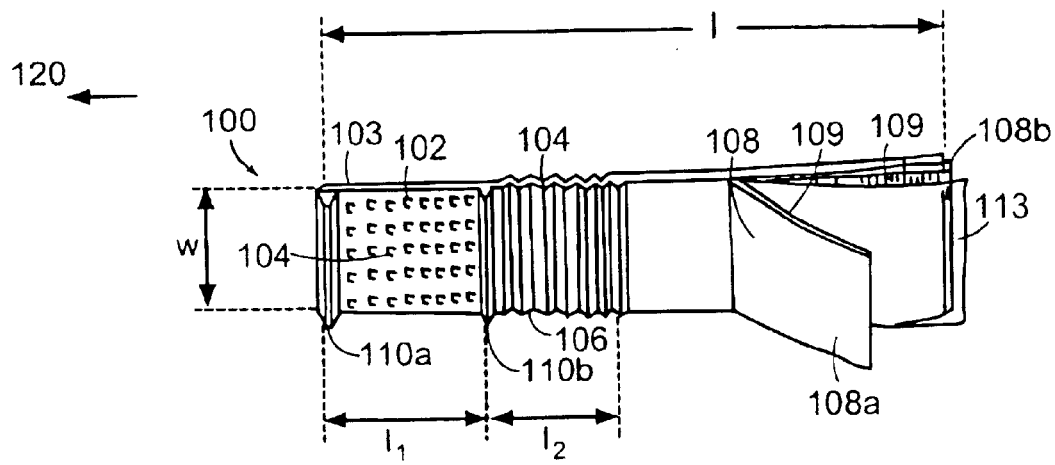
FIG. 1B is a perspective view of a fastening assembly.
Figure 1C:
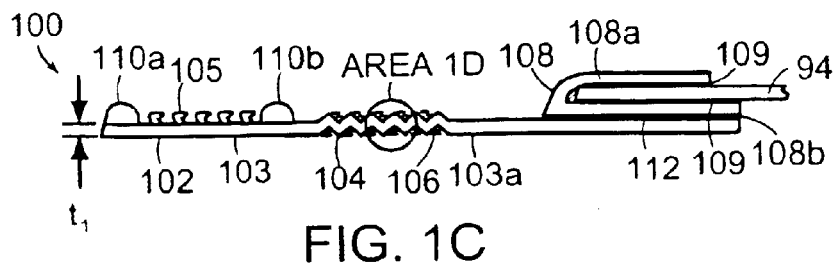
FIG. 1C is a side, cross-sectional view of the fastening assembly of FIG. 1B.
Figure 1D:
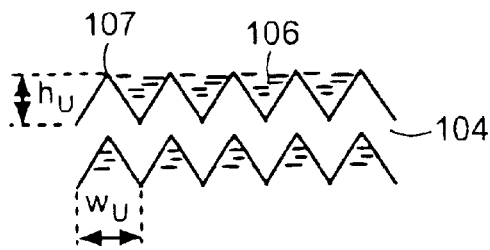
FIG. 1D is an expanded side, cross-sectional view of the area 1D of FIG. 1C.
Figure 1E:
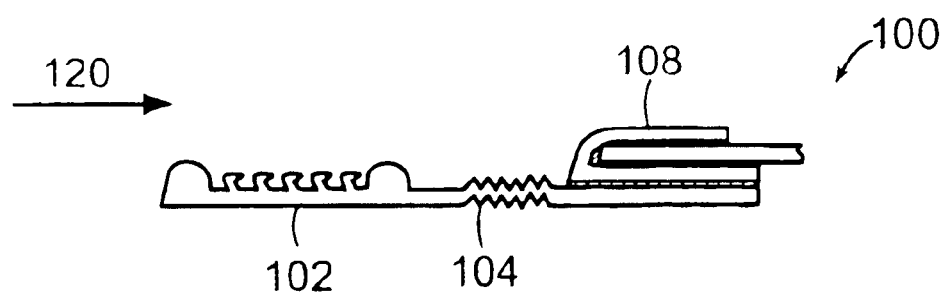
FIG. 1E is a side, cross-sectional view of the fastening assembly of FIG. 1B in compressed state.
Figure 1F:
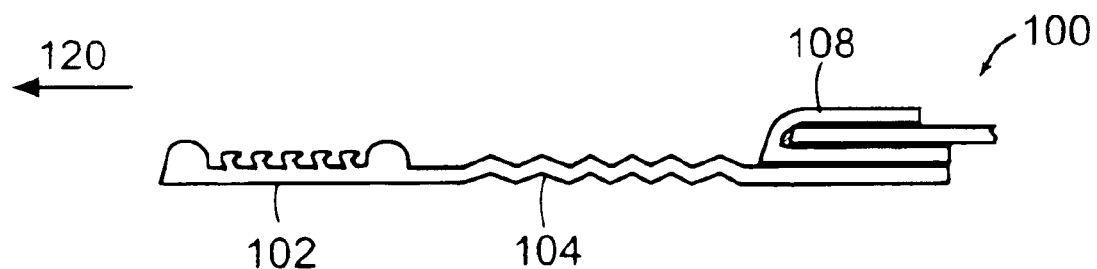
FIG. 1F is a side, cross-sectional view of the fastening assembly of FIG. 11B in extended state.
Figure 2A:
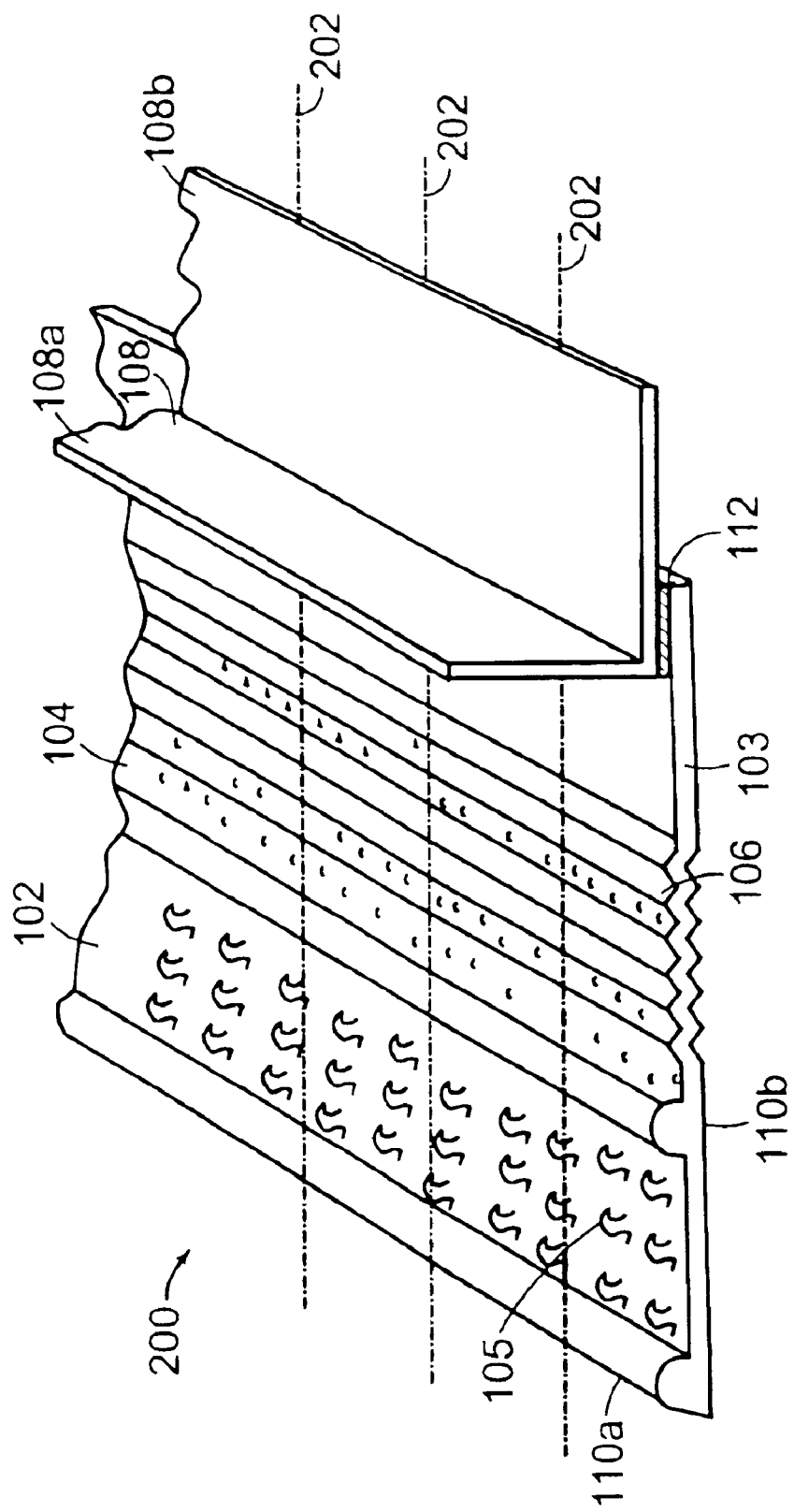
FIG. 2A is a perspective view of a continuous web from which the fastening assembly of FIG. 1B is cut.

The fastening assembly of FIGS. 1B and 1C is formed by cutting sections of a continuous web 200, shown in FIG. 2A, along the indicated lines 202. The continuous web 200 is advantageously formed by the process and apparatus illustrated in FIGS. 3A and 3B, now to be described.

Extruder barrel 51 melts and forces molten plastic 53 through a slot-form die 52. The extruded plastic enters nip 56 formed between base roll 54 and mold roll 55. Mold roll 55 contains a section with mold cavities 59 shaped to form hook-type fastener elements. Left and right of the section with the cavities 59 there are mold ridges 61a and 61b shaped to form the dams 110a and 110b, respectively. Adjacent to ridge 61b on the surface of the mold roll 55 and the opposing surface of the base roll 54 there are cooperating rib and groove sections 60 shaped to form undulations. The extruded plastic fills the hook cavities 59, ridges 61a and 61b, the undulating section 60, and the further base portion 103a, all as an integral resin member of a continuous web 200 (FIG. 3D).

Simultaneously with the molded plastic 53 forming the hook and undulating sections 102,104, respectively, a pre-formed web 108 enters the nip 56 and forms the tab section 108. In one embodiment, the web 108 is a non-woven material supplied by roll 40. The web 108 passes through guide rolls 41,42 and turning bars 43,44 and is twisted by ½ turn to form an L-shaped fold (FIG. 3C). The surface of the web forming the inside of the L-shaped fold is coated with a barrier layer 213 preventing the molded plastic from penetrating the non-woven web and fusing both sides of the folded web. The web enters the nip 56 so that one arm 108a of the L-shaped fold is inserted into slot 62 formed on the mold roll 55 and the other arm 108b overlaps partially and fuses with the molded plastic 53 forming the base 103 along the region 112 (FIG. 3D). The so-formed continuous web 200 travels about a segment of the periphery of mold roll 55 and is guided by guide rolls 57, 58 to post-processing stages 67 and 68. At post-processing stage 67 the inside surface of the L-shaped tab 108 is coated with an adhesive 109 and, optionally, a liner 113 is placed between the two arms 108a, 108b. Leg 108a is folded flat toward Subsequently the two arms 108a, 108b are folded down by turning bars 63,64 and the web passes through post-processing stage 68 where the undulations are compressed and doctor blades 71 apply an elastomeric resin 106 in the spaces between the undulations 107 and coat the tips of the undulations.

The elastomeric resin 106 is a thermoplastic polymer selected from the group consisting of thermoplastic elastomers, thermoplastic polyurethanes, elastomeric copolymers containing polyethylene terephthalate (PET), thermoplastic olefins, and natural or synthetic rubber. In one embodiment, the elastomeric resin 106 is composed of Santoprene®, having an elongation in the range of 50% to 300% and a recovery of at least 75%.

Figure 2B:
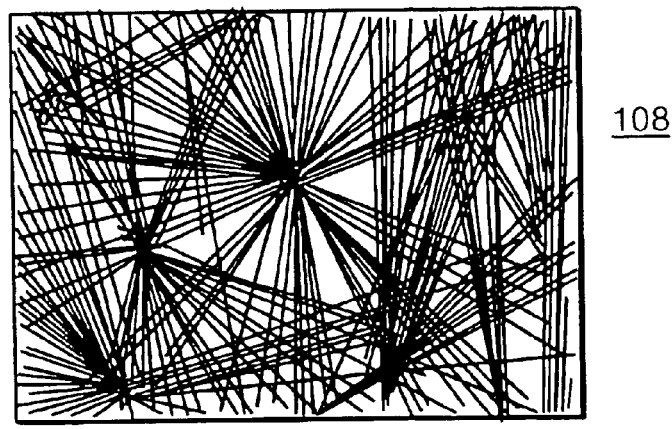
FIG. 2B is a schematic plan view of a preferred non-woven web for use in the tab of FIG. 1B.
Figure 2C:
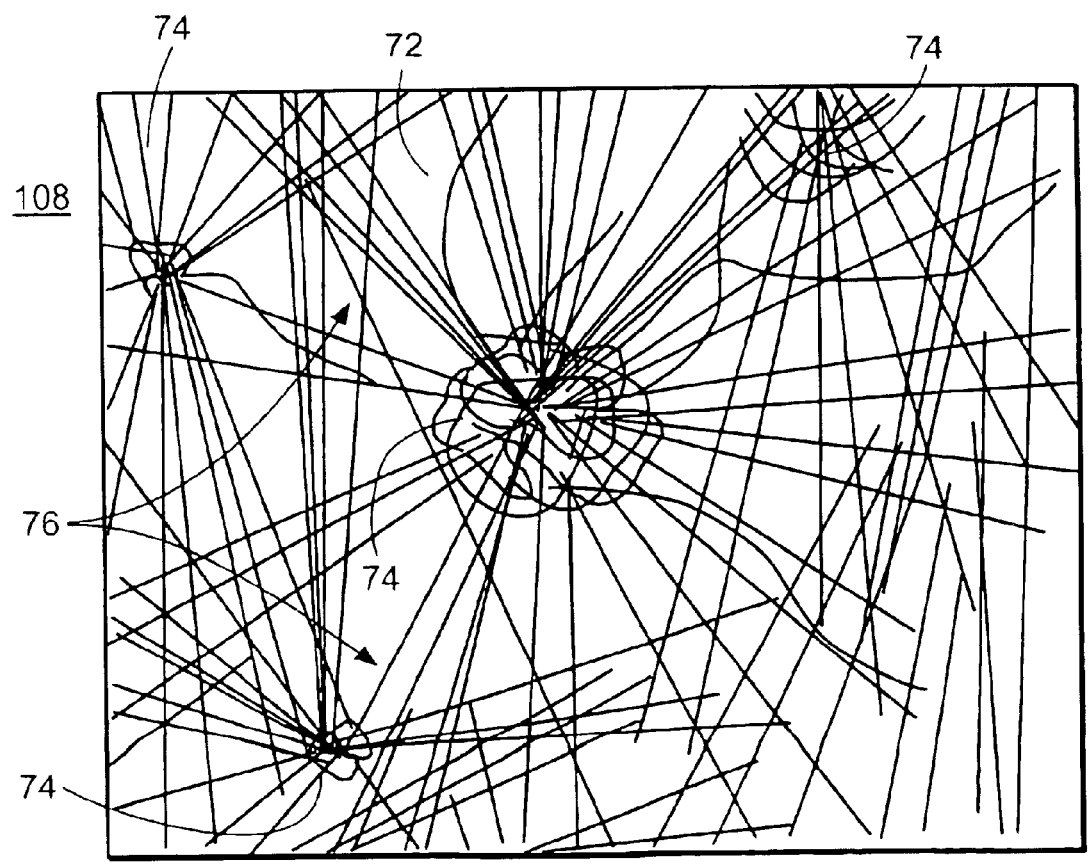
FIG. 2C is an enlarged schematic plan view of the face of the non-woven loop material shown in FIG. 2B.

The preformed web 108 may be a preformed non-woven or knitted loop material. In preferred embodiments, the non-woven loop material is a needled non-woven fabric, that has thickness of the order of 0.05 inch and basis weight of about 2 ounces or less per square yard (68 grams per square meter) (FIG. 2B). This very thin non-woven material 108 is dimensionally-stable and has relatively free hook-engageable fibers that extend from at least one side of a continuous, tangled mat of fibers 72 that form the web (FIG. 2C). These fibers have portions available to be engaged by loop-engageable hooks while portions of the fibers at both sides of the engageable portions are secured to the mat of fibers. In present, particularly preferred embodiments, the non-woven needled fabric comprises staple polyester yarns of between about 18 and 4 denier, preferably 6 denier. Following needling of a bat of these fibers, the product, is stretched longitudinally and transversely, to increase its area in excess of 100%, as much as 150% or more from its as-needled condition, following which fibers in the web that engage each other are bonded or adhered together, so that the web has significant tensile strength and the hook-engageable portions of the fibers are well anchored.

In such a fabric the individual fibers of the mat 72 follow no definite pattern as in a woven or knit product, but extend in various directions within the plane of the fabric mat. The hook-engageable fibers that extend from the non-woven product are of the same fibers that comprise the mat but extend beyond the general mass of the mat 72, out of its plane, generally from associated knots 74, in the form of well anchored loop trees.

In a particular embodiment employing needling followed by stretching, the fibers of the mat are held in their taut, straightened condition by a water-based, acrylic binder applied to the side of the mat opposite the loops to bind the mat fibers in their straight condition to stabilize the areal dimensions of the fabric, and to secure the loops at their associated knots. The binder generally ranges between 20 and 40% of the total weight of the fabric and in the presently preferred embodiments accounts for about one third of the total weight of the non-woven component.

A description of suitable needled and stretched, hook-engageable non-woven materials is found in U.S. Pat. No. 6,342,285 filed Sep. 3, 1997 entitled "Fastener Loop Material, Its Manufacture, and Products Incorporating the Material", and related U.S. Pat. No. 6,329,016, filed Mar. 3, 1999 entitled "Loop Material for Touch Fastening", the entire contents of both of which are hereby incorporated by reference.

Figure 3A:
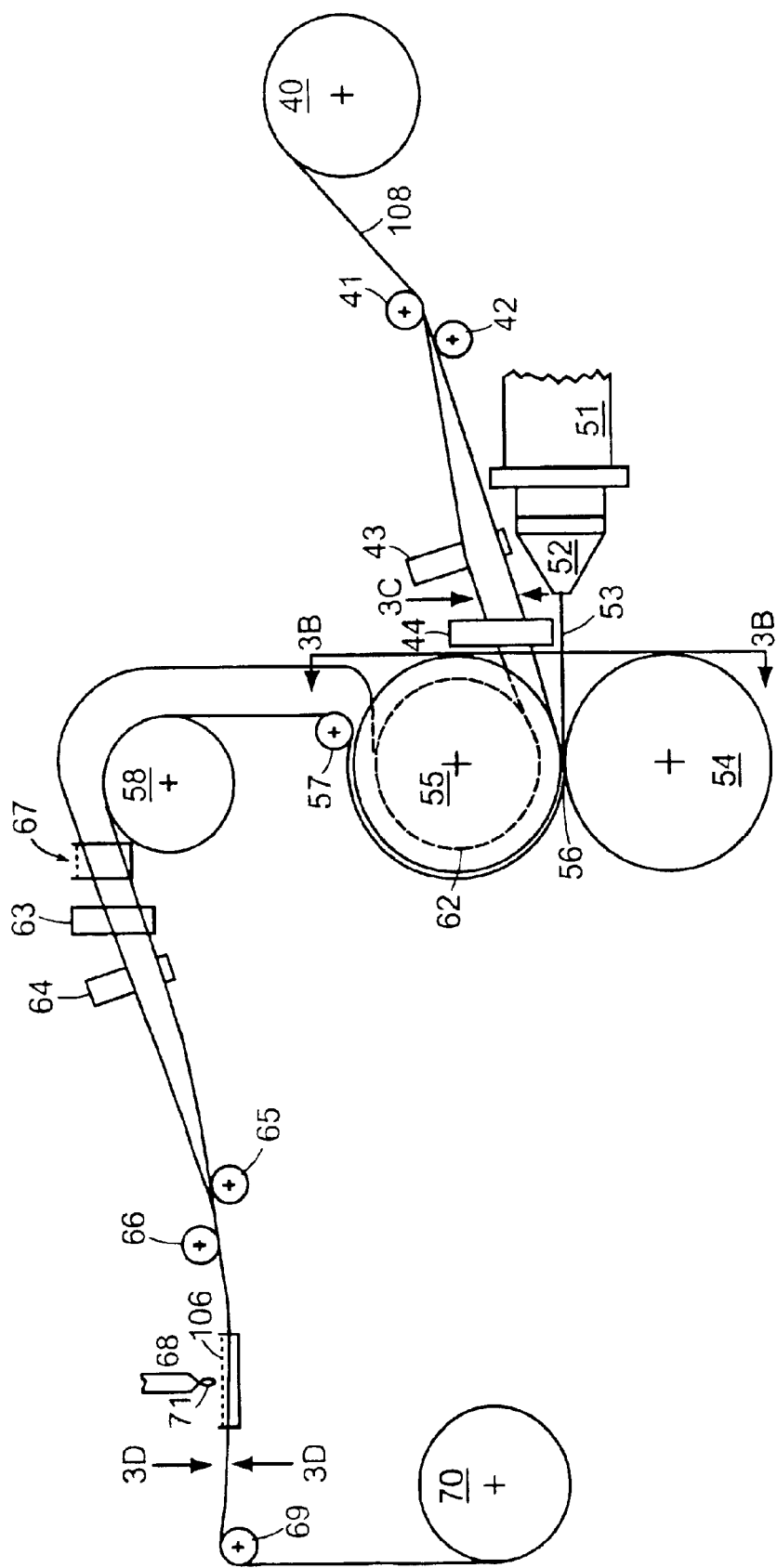
FIG. 3A is a side view of the apparatus forming the web of FIG. 2A.

For more detail about the general operation of in situ molding methods and apparatus as illustrated, e.g., in FIG. 3A, and for variations on the process, the reader is referred to U.S. Pat. No. 5,260,015 to Kennedy, et al., which discloses laminates made with loop materials.

Figure 4A:
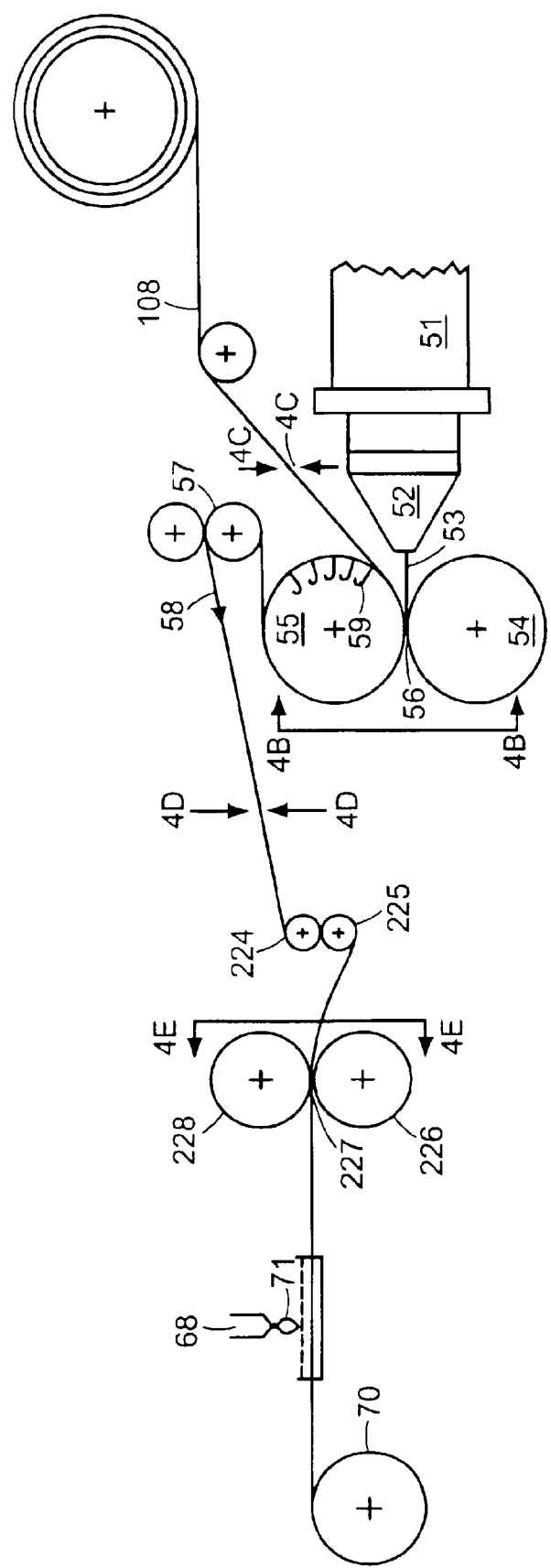
FIG. 4A is a side view of another apparatus forming the web of FIG. 2A.

The stretchable fastening assembly of FIGS. 1B, 1C may also be formed by the method and apparatus illustrated in FIG. 4A. Extruder barrel 51 melts and forces molten plastic 53 through a slot-form die 52. The extruded plastic enters the nip 56 between base roll 54 and mold roll 55. As was described above, mold roll 55 contains a section with mold cavities 59 shaped to form hook-type fastener elements and left and right of the section with the cavities 59 there are mold ridges 61a and 61b shaped to form the dams 110a and 110b, respectively. Adjacent to dam 10b a sheet-form portion of the plastic 153 is formed (FIG. 4D).

Simultaneously with the molded plastic 53 forming the hook and sheet-form sections a web 108 folded double enters the nip 56 to form the tab section 108. The inside surfaces of the folded web are separated by a film layer 212 or tape that prevents molded plastic from penetrating through the web and fusing both sides of the folded web. In one example, layer 212 comprises Teflon® tape. The entire backside of arm 108b of the folded web is in situ laminated to the base 103 along region 112 as the base is formed. The molded web travels about a segment of the periphery of mold roll 55 and guided by rolls 57, 225 and 224 enters a nip 227 formed between rolls 228 and 226 where the section with the undulations is formed. A heated portion 230 of the outside surface of rolls 226 and 228 has triangular or sinusoidal shaped undulations 60 which soften the sheet-form section 153 of the web and molds undulations 107 in the web 200. After the formation of the undulations the web passes through a post-processing stage 68 where the undulations are compressed and an elastomeric resin 106 is applied in the spaces between the undulations and on the undulations.

In another embodiment, shown in FIG. 5, the fastening assembly 100 features a fastener tape section 102, a stretchy undulating section 104 and a tab section 108, which is formed by folding a portion of the integrally formed base sheet 103. The fastening assembly of FIG. 5 is formed by cutting sections of a continuous web 300, shown in FIG. 5E, along the indicated lines 302.

Referring to FIG. 5A, a method of forming the continuous web 300 includes forming a continuous molded web featuring a section with hook-shaped fastener elements 102, dams 110a and 110b and an undulating section 104, as was described above. Next to the undulating section the base 103 of the web 300 is extended and a section 179 with reduced thickness is formed having fold lines 183, 184, 185 (FIG. 5B). The thickness of the molded web is reduced by inserting a ring 172 onto the mold roll 55 which reduces the thickness of the gap that establishes the thickness of this section (FIG. 5F). The molded web travels about a segment of the periphery of mold roll 55 and guided by rolls 57 and 58 enters a post-processing stage 180 where the base 103 is folded first upward along the fold line 183 then downward along line 184 and then horizontally along line 185 (FIG. 5C). The folding produces an inverted V-shaped fold 108 having arms 108a and 108b. The post-processing stage 180 includes a first block 181 having a longitudinally extending triangular-shaped step 188 and a second block 182 having a triangular-shaped groove 186 positioned on top of the triangular-shaped step 188. A narrow gap is formed between the groove 186 and the step 188 receiving and folding the web 300 along lines 183, 184, 185. The folded web 300 proceeds into next stage 190 where the two arms of the fold 108a and 108b are pressed and fused together forming a tab 108 integral with the base 103. Stage 190 includes a base block 191 supporting the web on its surface and a heated block 192 having a slit 193 receiving and pressing the arms 108a, 108b of the fold together (FIG. 5D). The heat melts the plastic sufficiently to fuse the two arms together. The web 300 then continues into stage 68 where the undulations are compressed and an elastomeric resin is applied in the spaces between the undulations and on the undulations.

Figure 6B:
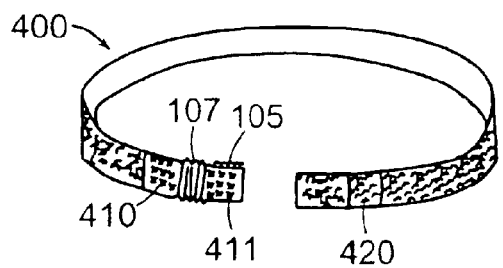
FIG. 6B is perspective view of a belt-type fastening assembly.
Figure 6A:
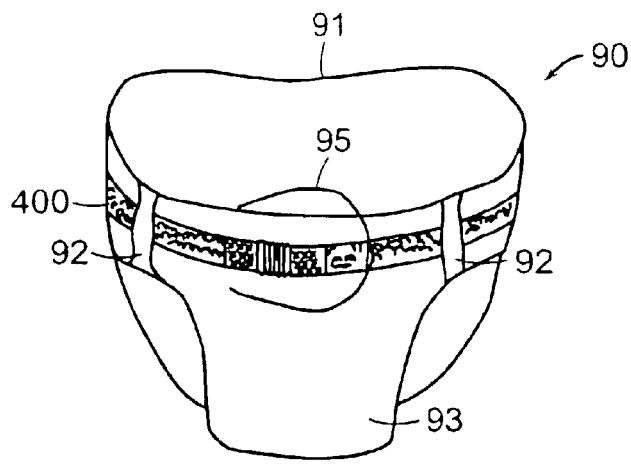
FIG. 6A is a perspective view of a diaper comprising a belt-type fastening assembly.

Referring to FIG. 6A, the back side 91 of a diaper 90 is attached to the front side 93 by a fastening assembly forming a belt 400. Belt 400 passes through loops 92, surrounds the diaper 90 and forms a closure 95. Referring to FIG. 6B, the belt 400 includes a fastening section 410 and an elongated section 420. The fastening section 410 includes hooks 105, dams 110a, 10b and undulations 107 providing elasticity to the fastening section 410 (FIG. 6D). The back side 411 of the fastening section 410 has embossing or other surface patterns for grasping by the user. The elongated section 420 comprises a non-woven web 412 which has a portion fused to a portion of the fastening section along region 112.

Figure 6C:
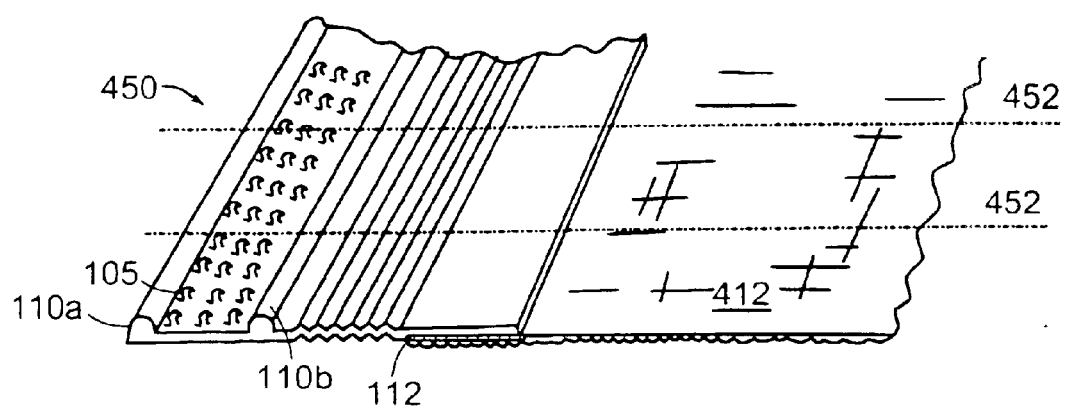
FIG. 6C is a perspective view of a continuous web 450 from which the belt-type fastening assembly of FIG. 6B is cut.
Figure 6D:
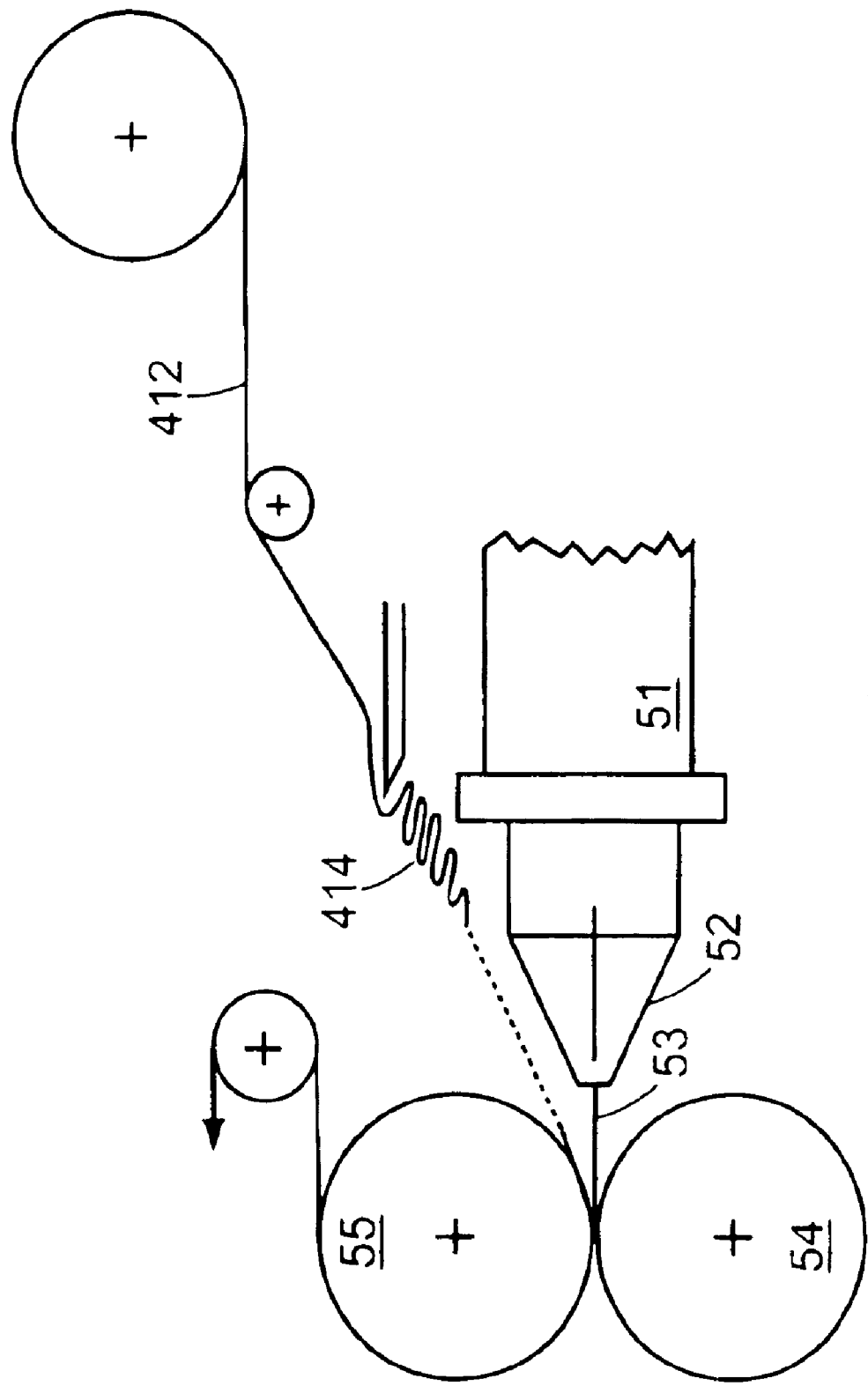
FIG. 6D is a side view of an apparatus-folding web 412 of FIG. 6C and in situ laminating it to a fastening section.
Figure 6E:
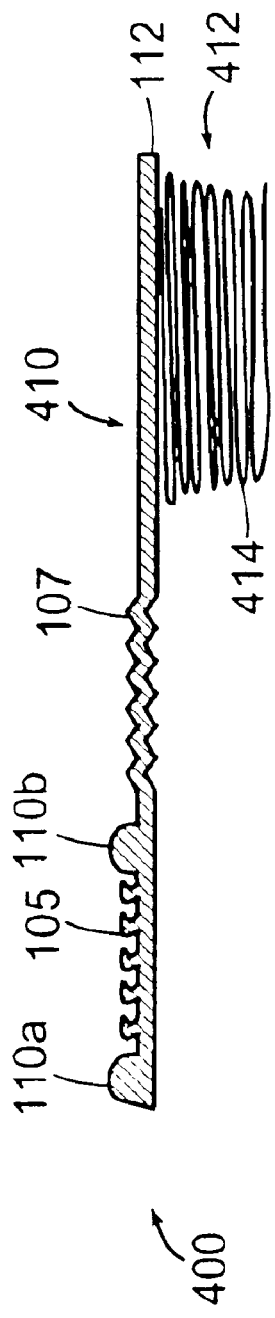
FIG. 6E is a diagrammatic cross-sectional side view of the web 450 of FIG. 6C with a folded web 412.

The belt 400 is formed by cutting segments of web 450, shown in FIG. 6C, along indicated lines 452. The web 450 is formed with the method and apparatus shown in FIG. 3A or FIG. 4A. The non-woven web 412 is folded forming multiple folds 414, as shown diagrammatically in FIGS. 6D and 6E, and the folded web is introduced into the nip area 56 where it is laminated in situ to a portion of the molded fastening section. After the formation of the fastening section, web 450 is cut along lines 452 and folds 414 is unfolded resulting in the elongated section 450 forming the belt 400. Other features and advantages of the invention may include one or more of the following.

Figure 7A:
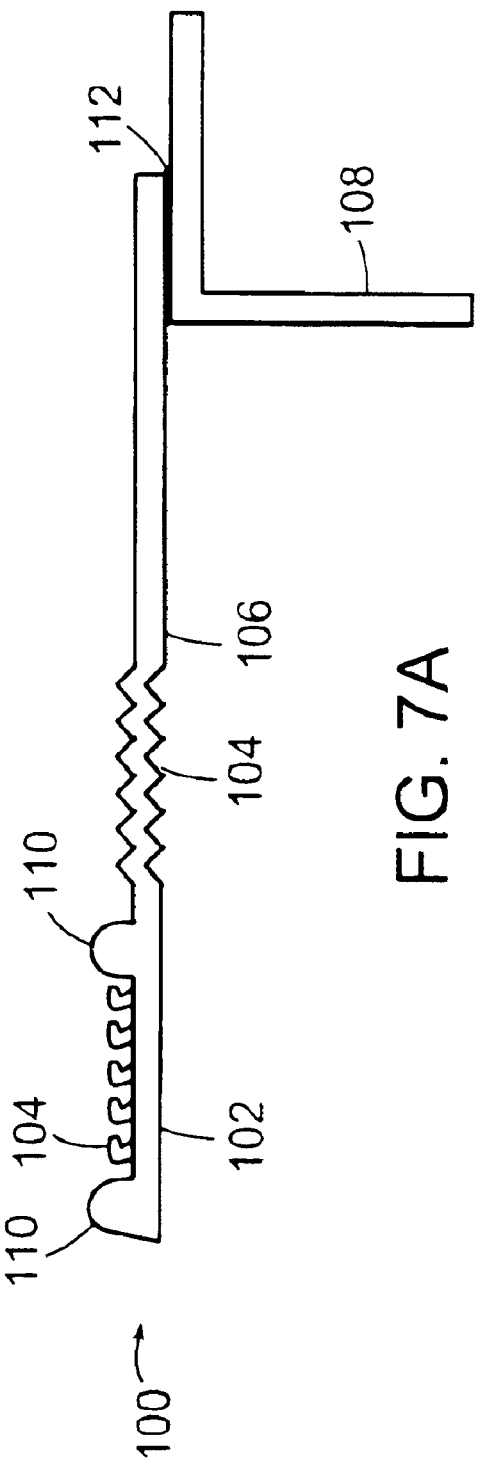
FIG. 7A is a diagrammatic cross-sectional side view of another fastening assembly.

The folded web 108 may be laminated onto the surface of the fastener tape opposite the surface from which the hook-shaped fastener elements extend (FIG. 7A).

The adhesive 109 may be activated by ultrasound or ultraviolet light, in which case no liner 113 is applied. Further the tab 108 may be provided without the adhesive 109 and an adhesive layer may be applied on the surface of the diaper where the fastening assembly is attached during the diaper assembly operation.

Figure 8:
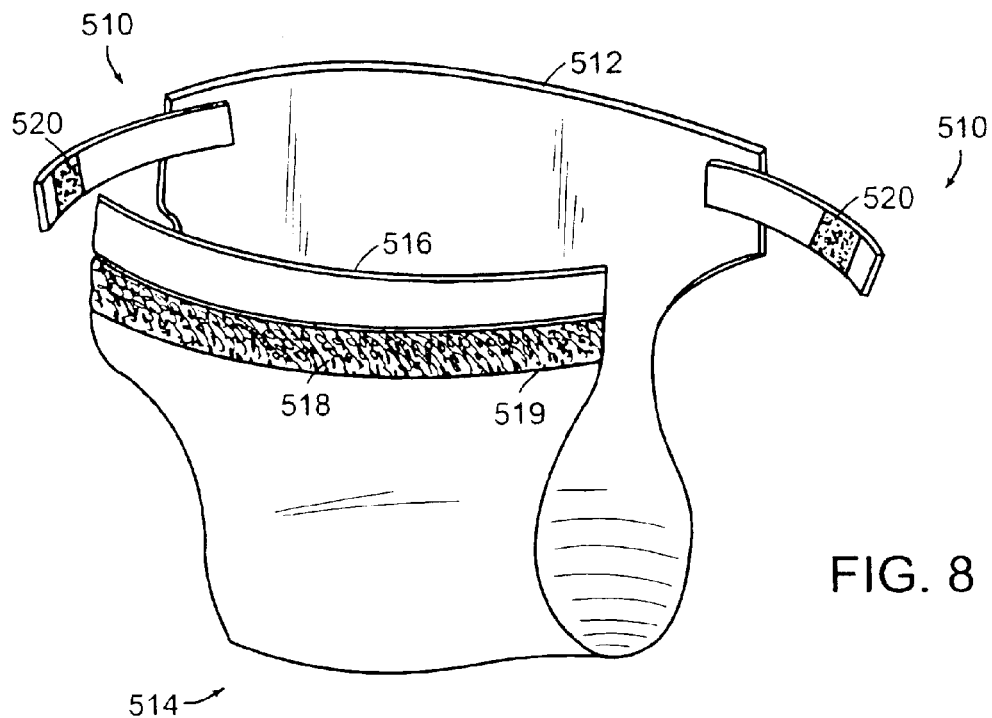
FIG. 8 is a perspective view of a diaper including fastener tabs, according to the invention.

Referring to FIG. 8, a fastener tab 510 is used to secure two components together, e.g., two fastener tabs 510 are shown securing a back 512 of a diaper 514 to a front 516 of the diaper. Fastener tab 510 is attached to diaper back 512 by, e.g., adhesive, and is releasably secured to diaper front 516 by engaging a hook-bearing fastener strip section 520 of tab 510 with a receiving region 518 on the front 516 of diaper 514. Receiving region 518 includes, e.g., hook-engageable loops 519.

Figure 9A:
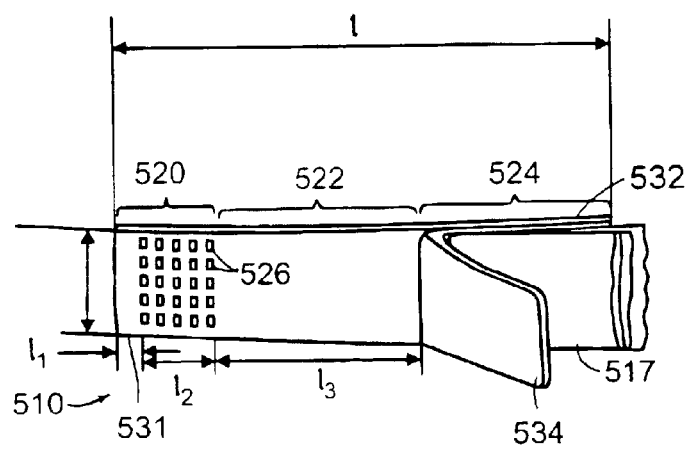
FIG. 9A is a perspective view of the fastener tab of FIG. 8.
Figure 9B:
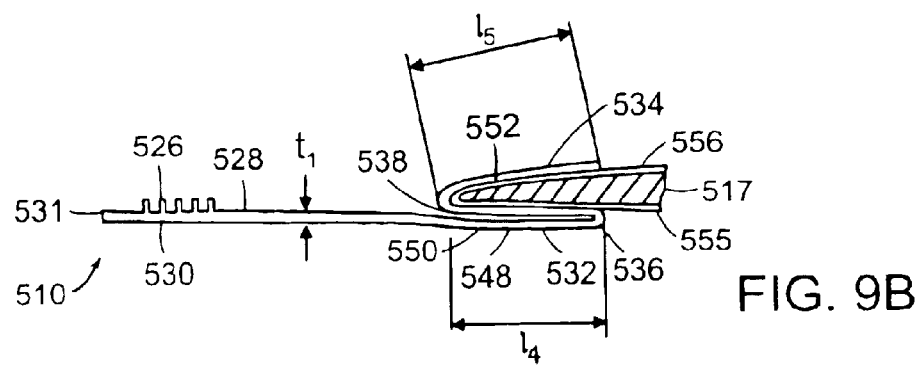
FIG. 9B is a side view of the fastener tab of FIG. 9A.

Fastener tab 510, shown in FIGS. 9A and 9B, is formed as a flexible, unitary strip of thermoplastic resin, e.g., polypropylene. Tab 510 includes fastener strip section 520, a central strip section 522, and an attachment section 524. Sections 520, 522 and 524 are integrally formed in a single molding/calendaring operation, as described below. Tab 510 includes a continuous base portion 530, and fastener strip section 520 includes a plurality of loop-engageable hooks 526 integrally molded with and extending from a surface 528 of base portion 530. Referring to FIG. 10, hook protrusions 526 are molded in a high density array, as described below, each in the shape of a loop-engageable hook, with, e.g., a crook 527 or mushroom form (not shown). Alternatively, hooks 526 can be initially molded as pre-forms, with the crook or mushroom shapes or other loop-engageable configurations being formed in a post-forming operation, e.g., after the initial molding process. In one example, the hooks are of CFM-29 designation, as previously described. Hooks 526 can be arranged in alternate rows, the hooks facing in opposite directions, as shown in FIG. 10, or hooks 526 can face in the same direction.

Fastener strip section 520 terminates in a graspable tip portion 531 devoid of hooks which the user grasps to disengage tab 510 from receiving region 518 of diaper 514 by a peeling motion. Central strip section 522 is devoid of hooks and extends between fastener strip section 520 and attachment section 524 to provide a flexible, manipulatable support for fastener section 520. Attachment section 524 includes a first leg 532 and a second leg 534 for attaching to opposite sides 555, 556 (FIG. 9B) of a diaper or other substrate 517. An adhesive 548 on the inside surfaces 550, 552, respectively, of legs 532, 534 is used to attach tab 510 to substrate 517.

Referring to FIG. 11A, legs 532 and 534 are formed by folding base portion 530. Base portion 530 in attachment section 524 includes a first portion 570, a second portion 572, and a third portion 574. Between the first and second portions 570, 572 is a hinge 576, and between the second and third portions 572, 574 is a hinge 578. To form legs 532 and 534, second portion 572 is folded over first portion 570 at hinge 576, forming leg 532, as shown in FIG. 11B. Third section 574 is then folded over second portion 572 at hinge 578, forming leg 534, as shown in FIG. 9B. First and second portions 570, 572 have a reduced thickness, which form recessed surfaces 580, 582, respectively. First portion 570 is adhered to second portion 572 by an adhesive 584, e.g., a rubber based pressure sensitive adhesive, applied to surface 580 or 582 or both. Alternatively, portions 570, 572 are adhered by heat staking, ultrasonic bonding or rf welding.

Referring again to FIGS. 9A and 9B, tab 510 has a base thickness, $t_1$, of, e.g., about 0.004 to 0.006 inches, a width, w, of, e.g., about 0.75 to 2 inches, and an overall length, l, of, e.g., about 4 inches. The graspable tip portion 531 of fastener section 520 has a length, $l_1$, of, e.g., about 0.25 inches, and the remainder of fastener section 520 has a length, $l_2$, of, e.g., about 0.875 inches. Central strip section 522 has a length, $l_3$, of, e.g., about 0.75 inches. First leg 532 has a length, $l_4$, of, e.g., about 0.875 inches and second leg 534 has a length, $l_5$, of, e.g., about 0.75 inches.

Figure 12:
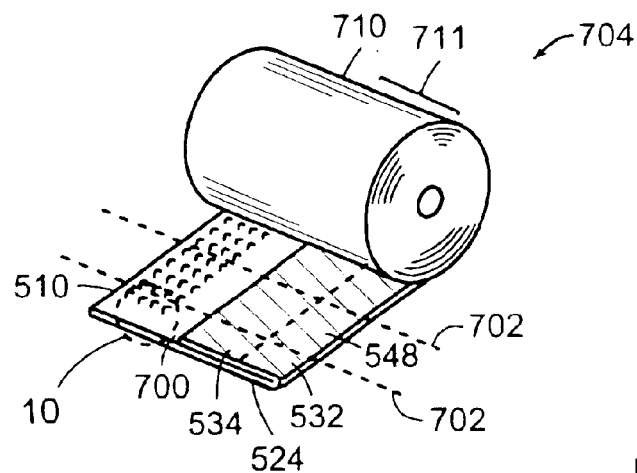
FIG. 12 is a perspective view of a continuous web of fastener tab material stored in roll form.
Figure 13A:
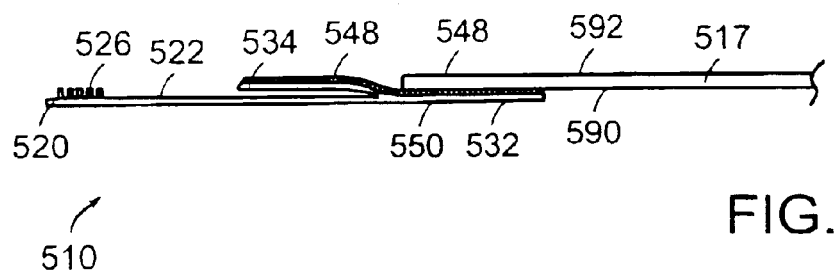
FIG. 13A is a side view of the fastener tab of FIG. 9A shown partially attached to a substrate.
Figure 13B:
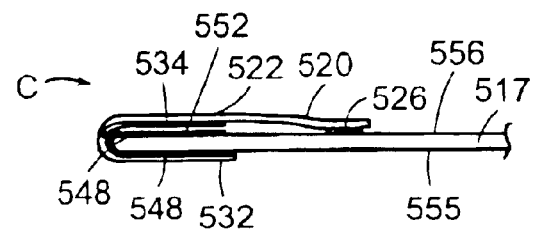
FIG. 13B is a side view of the fastener tab of FIG. 9A shown attached to a substrate with the fastener tab in a protected position.
Figure 13C:
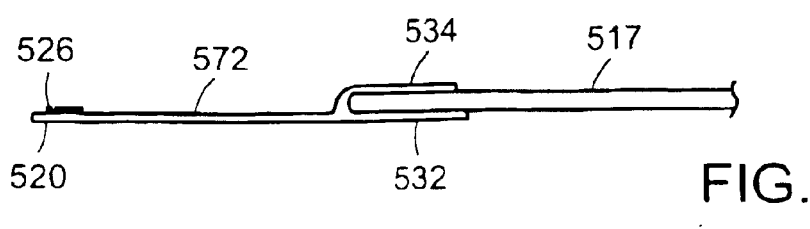
FIG. 13C is a side view of the fastener tab of FIG. 9A shown attached to a substrate and in position for use.

Referring to FIG. 12, fastener tabs 510 are initially formed as a continuous web 700 from which individual fastener tabs are separated along the indicated lines 702. Web 700 is provided in a roll form 704 with attachment section 524 in the partially folded position of FIG. 11B. To limit adherence of adhesive 548 to backside 710 of web 700 and thus aid in release and unrolling of web 700, backside 710 is treated with a release coating, e.g. a fluorine or silicone based coating, in an area 711 that corresponds to adhesive 548. In use, referring to FIGS. 13A–13C, an individual tab 510 is removed from web 700, e.g., by cutting web 700 along line 702, and attached to the diaper or other substrate 517 by contacting the adhesive bearing inside face 550 of leg 532 to one side 555 of the substrate while tab 510 is in the partially folded position of FIG. 11B. Fastener strip section 520 and central strip section 522 are then folded in the direction of arrow C (FIG. 13B) until hooks 526 of fastener strip section 520 contact the opposite side 556 of substrate 517. This folding motion of the unattached portion of tab 510 brings the adhesive bearing surface 552 of second leg 534 into contact with the opposite side 556 of substrate 517, and hooks 526 into loose engagement with the material of substrate 517. Alternatively, adhesive 548 is omitted, and another fastening technique, e.g., heat staking or ultrasonic or rf welding using the self-adhesive properties of the surfaces being joined, is employed to attach legs 532 and 534 to substrate 517.

With attachment legs 532 and 534 attached to substrate 517, and fastener strip section 520 and central strip section 522 folded over substrate 517, tab 510 is in a protected position for further processing, packaging, and shipping of the diaper or other substrate. A user of the diaper or substrate unfolds fastener strip section 520 (FIG. 13C) to present hooks 526 for use in securing the diaper about a wearer, or otherwise using the substrate for its intended purpose.

Figure 14C:
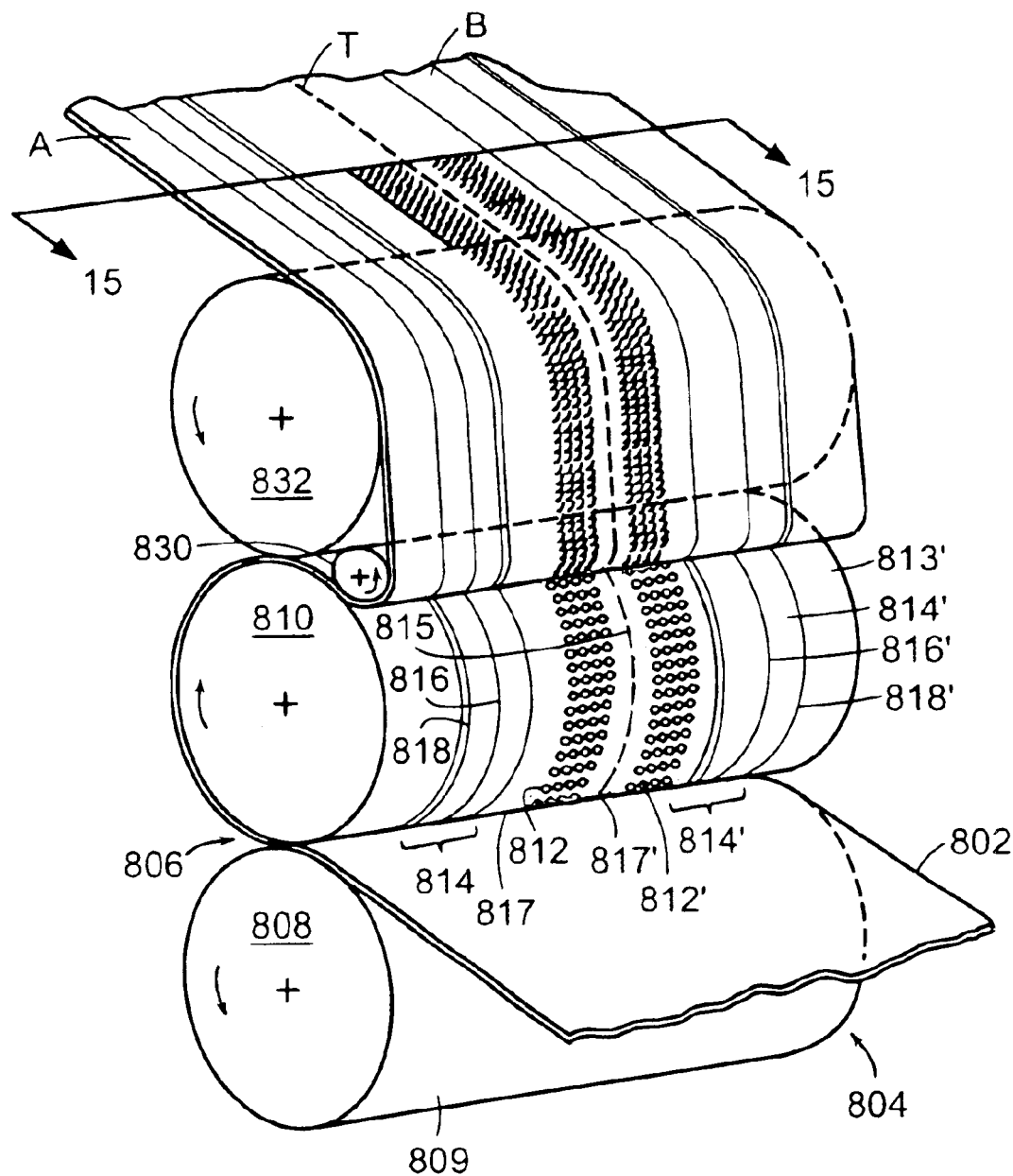
FIG. 14C is a perspective view of the molding/calendaring assembly of FIG. 14B shown with a guide roll.
Figure 15:
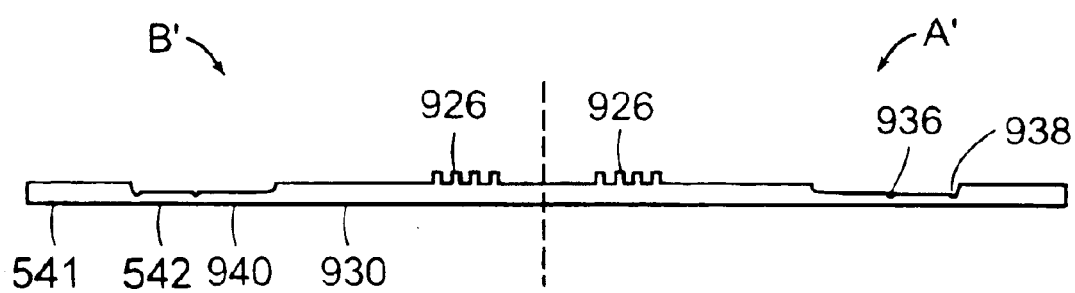
FIG. 15 is an end view of the continuous web produced by the molding/calendaring assembly of FIG. 14B.

Referring to FIGS. 14A–14C, continuous web 700 is formed by an extrusion apparatus 801 including a molding/calendaring assembly 303 and post-processing stages 805. Assembly 803 includes an extruder barrel 800, a slot-form die 804, a base roll 808, a mold roll 810, a take-off roll 830, and a guide roll 832. Referring particularly to FIG. 14B, mold roll 810 includes, e.g., two sets of side-by-side tab forming formations, A and B, which produce two bands A', B' of tabs 510 (see FIG. 15). Mold roll 810 has a narrow ring 815 of increased diameter shaped to create a separation groove T (FIG. 15) between bands A' and B'. Groove T is an integral, relatively thin, rupturable joint which permits easy separation of bands A' and B'. Roll 810 has two sections 817, 817' adjacent ring 815 that define mold cavities 812, 812', respectively, shaped to form hook-type fastener elements 526. Next to mold cavity sections 812, 812', mold roll 810 has outer calendaring surfaces 813, 813' including sections 814, 814' of increased diameter that form reduced thickness sections 580, 582 in tab 510. Near the center and edge of sections 814, 814' are rings 816, 816' and 818, 818' on the mold roll 810, shaped to form hinges 576, 578, respectively. Base roll 808 is provided with a relatively smooth outer surface 809, e.g., to provide a tab surface suitable to receive a release coating. Rolls 808 and 810 are spaced a given distance 820 to form base 530 of a desired thickness.

In use, extruder barrel 800 melts the resin and forces the molten plastic through slot-form die 804, to form a sheet-form extrudate of molten plastic 802. The extruded plastic 802, while still molten, enters a nip 806 formed between base roll 808 and mold roll 810. Due to pressure applied at the nip by rolls 808, 810, molten resin is forced into hook cavities 812, and, by filling the gap 820 between the rolls 808, 810, forms base portion 530 and the various recessed and hinged portions, all as an integral, continuous, thermoplastic web.

As shown in FIGS. 14A and 14C, upon exiting nip 806, the formed web travels about a segment of the periphery of mold roll 810 while it cools (mold roll 810 having provision for internal cooling) and then, with the aid of take-off roll 830, the web disengages from the mold roll in a peeling action with the hook-form elements undergoing temporary elastic deformation as they exit from the mold cavities. Then, guided by guide roll 832, the web enters a post-processing stage 850 where adhesive 584 is applied to one or both of surfaces 580, 582.

The molded web then passes to a second post-processing stage 860, where the continuous webs of fastener tab profiles A' and B' are separated along line T. Further processing of the symmetrical webs A' and B' is identical. For simplicity, further treatment of a single fastener tab profile will therefore be described. The web next passes through stage 870 where the web is folded along the relatively thin hinge line 576 which lies between sections 570, 572 until sections 570, 572 are adhered together. Alternatively, after the web separation of stage 860 and the folding of stage 870 are performed, sections 570, 572 are joined by heat staking, ultrasonic bonding or rf welding, employing the adhesive qualities of the thermoplastic resin of which the tabs are formed.

The molded, folded web then passes to post-processing stage 880 where adhesive 548 is applied to surfaces 550, 552. Alternatively, stage 880 and the application of adhesive 548 are omitted, and adhesive or other fastening techniques are used after shipment of the fastener tabs 510 to the diaper manufacturer, prior to attachment to a diaper, e.g. fastener tab 510 is attached to a diaper or other article without the use of adhesive, e.g., by heat staking or ultrasonic or rf welding, using the self-adhesive properties of the surfaces being joined. The continuous web of fastening tab material is then wound into roll form 704 (FIG. 12) at post-processing stage 890 for shipment to diaper manufacturers.

Figure 16:
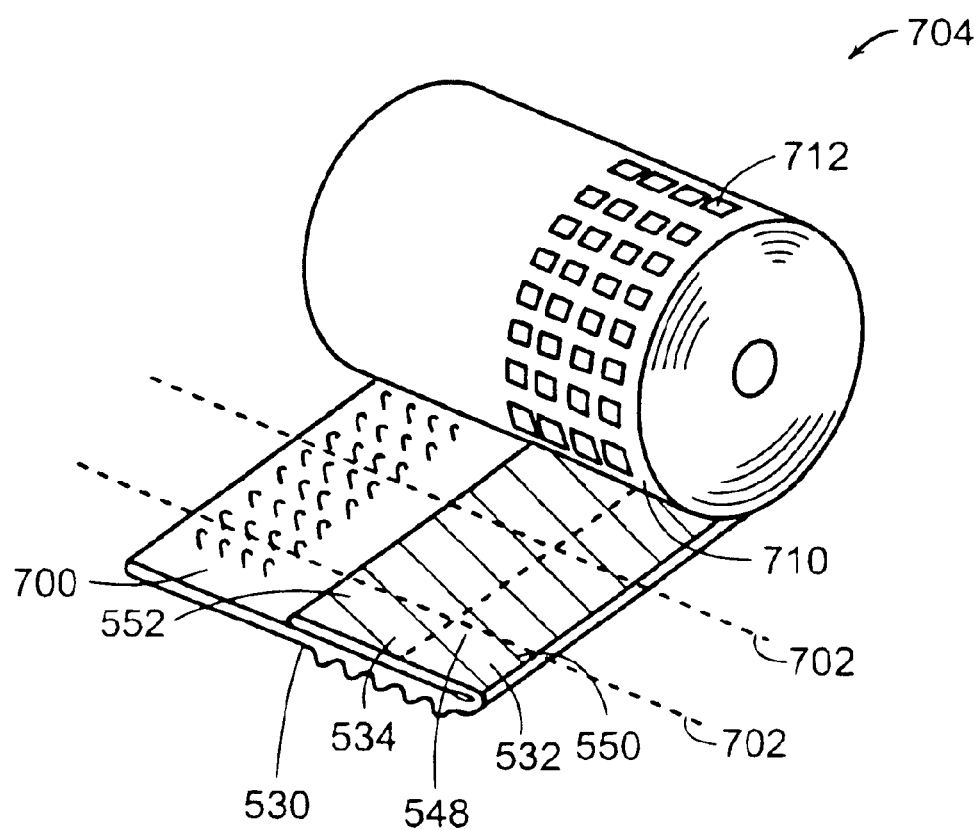
FIG. 16 is a perspective view of an alternative embodiment of a continuous web of fastener tab material.

For example, as shown in FIG. 16, a distribution of protruding formations 712 is formed on backside surface 710 of the web to reduce the area of contact between adhesive 548 and the backside surface 710 to aid in release and unrolling of the web. To form formations 712, the outer surface 809 of base roll 808 is provided with a grained texture, not shown, suitable to form molded formations 712.

Referring to FIGS. 17A and 17B, a fastener tab 510' includes a first hinge line 537', a second hinge line 536' separating a thinned portion 540' into first and second parts 542' and 544', respectively, and a third hinge line 538'. At a post-processing stage, e.g., after the molding/calendaring process, a second attachment leg 534' of tab 510' is formed by applying adhesive 541' along surface 543' of first part 542' or surface 545' of second part 544' or both, and folding thinned portion 540' at second hinge line 536' to adhere first part 542' to second part 544'. Alternatively, adhesive 541' is omitted and first part 542' is joined to second part 544' by heat staking or ultrasonic bonding, using the self-adhesive properties of the surfaces being joined. The portion of base 530' between third hinge line 538' and free end 546' forms a first leg 532'. Second leg 534' is folded open by folding about first hinge line 537' for further processing, storage, and shipping or folded closed about third hinge line 538' for attachment to a substrate.

In another embodiment, shown in FIG. 18, fastener tab 610' has first and second integrally formed legs 632', 634', produced without folding, and hinge lines 632', 634'. Referring to FIG. 19, leg 634' is molded using a mold roll 608' with a leg forming mold cavity 633' to create second leg 634' and mold ridges 616', 618' which form hinge lines 636', 638', respectively. Leg 632' is formed by the calendaring effect, using a process similar to that described above. Second leg 634' opens by folding about first hinge line 636' for further processing, storage, and shipping or closes by folding about second hinge line 638 for attachment to substrate. In this embodiment, second leg 634' typically has a length, l, of, e.g., about 0.25 inches.

Figure 20A:
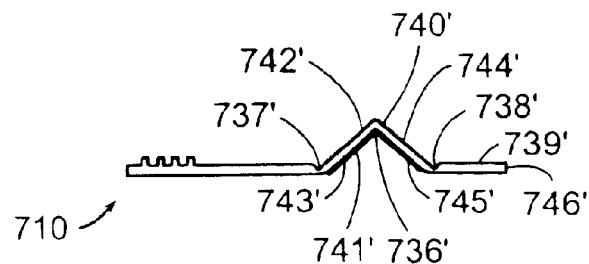
FIG. 20A is a side view of an additional alternative embodiment of a fastener tab shown in an unfolded state.
Figure 20B:
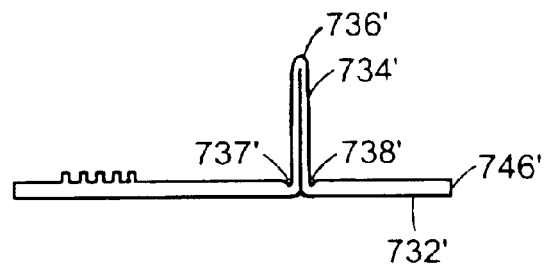
FIG. 20B is a side view of the fastener tab of FIG. 20A shown in a folded state.
Figure 21:
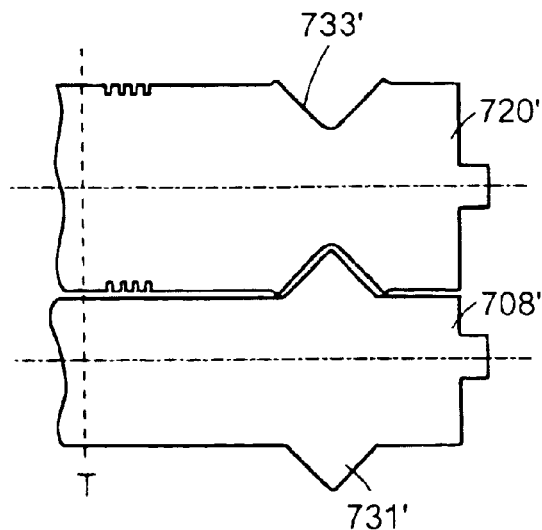
FIG. 21 shows a mold roll and base roll for forming the fastener tab of FIG. 20A.

Referring to FIGS. 20A and 20B, a fastener tab 710' includes a first hinge line 737', a second hinge line 736' separating a thinned portion 740' into first and second parts 742' and 744', respectively, and a third hinge line 738'. In this embodiment, thinned portion 740' is molded/calendared in a partially pre-folded condition. To form the partial pre-fold, as shown in FIG. 21, a mold roll 720' has a recessed portion 733' and a pressure roll 708' has a corresponding raised portion 731' that, acting together in the above described molding/calendaring process, produce a thinned portion 740' having an inverted V-shaped fold. At a post-processing stage, e.g., after the molding/calendaring process, a second attachment leg 734' of the tab is formed by applying adhesive 741' along surface 743' of first part 742' or surface 745' of second part 744' or both, and folding partially pre-folded thinned portion 740' at second hinge line 736' to adhere first part 742' to second part 744'. Alternatively, adhesive 741' is omitted and first part 742' is joined to second part 744' by heat staking or ultrasonic bonding, using the self-adhesive properties of the surfaces being joined. The portion 739' between third hinge line 738' and free end 746' forms first leg 732'. Second leg 734' is folded open by folding about first hinge line 737' for further processing, storage, and shipping or folded closed about third hinge line 738' for attachment to a substrate.

FIGS. 22A and 22B illustrate stages of the side-by-side simultaneous production of six fastener tabs. The dimensions are not to scale, and particularly, the thickness of the material has been exaggerated for ease of illustration. Referring to FIG. 22A, fastener tab pre-forms (TP1–TP6) are initially produced as an integral tape 900. Each tab pre-form has a graspable tip portion 902, a fastener element bearing portion 904 and a tab attachment portion 906. Underlying the entire width of web 900 is a backing web 908. Tip portion 902 and fastener element bearing portion 904 are extruded and molded integrally from the same material onto web 908. The heat and pressure of the molding operation, described below, laminates the molded tip and fastener element-bearing portions 902, 904 onto web 908 so that the materials form integral tape 900.

In one example, each of the six tab pre-forms TP1–TP6 has a tip portion 902 with a width, $w_t$, of approximately ⅛ inch (3.2 mm), a fastener element-bearing portion 904 with a width, $w_f$, of approximately ⅝ to ⅞ inch (15.9–22.2 mm), and a tab attachment portion 906 with a width, $w_a$, of approximately 2 and ⅝ to 3 and ⅛ (66.7–79.4 mm).

Underlying web 908, for example, is a film of polypropylene or polyethylene or a spun-bond nonwoven web of polypropylene or polyethylene or a laminate of a combination of these materials. Web 908 can also be of other materials such as an elastically stretchy nonwoven loop material that is releasably engageable by fastener element-bearing portion 904. In one example, the thickness, $t_w$, of web 908 is approximately 0.003–0.006 inch (0.08–0.15 mm) the molded, laminated material of the tip and fastener element-bearing portions 902, 904 can locally add an additional thickness of approximately 0.001 inch (0.03 mm) to the $t_w$ dimension in those areas.

Tape 900 is initially slit along lines C2 and C4 to provide three fastener tape pre-form webs, each including a pair of fastener pre-forms across its width, i.e., pairs TP1–TP2, TP3–TP4, and TP5–TP6 are formed. As the fastener pre-forms are further processed, each of the pairs are slit along lines C1, C3 and C5, leaving individual pre-forms PT1–PT6. Each individual pre-form is folded and partially adhered to itself in a process similar to that described above with reference to FIGS. 11A and 11B. The resulting fastener tabs T1–T6 are illustrated in FIG. 22B. Again, the dimensions are not to scale and, particularly, the thickness of the base portion and folded portions is exaggerated for ease of illustration. Fastener tab products T1–T6 are shown with attachment flap 910 in a partial closed position, ready for attachment to e.g., a garment or substrate, in the manner described above with reference to FIG. 9B. Also, each continuous length of fastener tab products T1-T6 can be rolled for storage with or without a layer of adhesive provided for attachment, in the manner described above with reference to FIGS. 12 and 16.

The method of producing the side-by-side preform tab of FIG. 22A employs the same basic principles of that described above with reference to FIG. 14C. However, the addition of the backing web, eliminates the need to provide extruded molten material over the entire width of the forming nip. Instead, the exposed surface of the tip portion 902 and the fastener elements of the fastener element-bearing portion 904 are formed as bands of molten material introduced into the nip simultaneously with the backing material 908. Such a technique of in-situ, laminating and molding bands or islands of material to an initially separate, second material is discussed in greater detail in co-pending U.S. application Ser. No. 09/808,395, filed Mar. 14, 2001 and entitled "Hook and Loop Fastening", the entire contents of which is hereby incorporated by reference.

Other features and advantages of the invention will be realized from the disclosure and drawings, and are within the scope of the following claims.

What is claimed is:

1. A method of forming a fastening assembly comprising:
 delivering a thermoplastic resin to a rotating mold roll;
 on the roll, continuously molding a fastener sheet having a base and a multiplicity of molded fastener element stem portions extending integrally from the base in a fastening section of the base lying generally in a plane; while
 continuously molding a non-planar undulation in which the base extends out of its plane to form a peak that extends in a forming direction with opposite major surfaces of the base remaining generally parallel, the undulation being elastically deformable to enable said base to stretch laterally upon application of a lateral tensile force to the fastening assembly.

2. The method of claim 1, wherein the base, as molded, has multiple, parallel undulations, each undulation forming a peak.

3. The method of claim 2, wherein said undulations are disposed in a region adjacent said fastener elements.

4. The method of claim 2, wherein said undulations are molded integrally with the fastener section.

5. The method of claim 2 further comprising filling an area between adjacent peaks with an elastomer.

6. The method of claim 1 which the undulation is formed by a mating groove and channel of a pair of rolls defining a nip in which the base is formed.

7. The method of claim 1 further comprising coating the undulation with an elastomer.

8. The method of claim 7 in which the elastomer is selected from the group consisting of thermoplastic elastomers, thermoplastic polyurethanes, elastomeric copolymers containing polyethylene terephthalate PET, thermoplastic olefins, and natural or synthetic rubber.

9. The method of claim 1 in which the fastener section is molded of resin selected from the group consisting of polyester, polyethylene, polypropylene, polyamide and copolymers and alloys thereof.

10. The method of claims 1 further comprising forming a tab joined with said base, the tab extending laterally from the undulation along a lateral margin of the fastener assembly opposite a second lateral margin more nearly adjacent the fastening section, the tab comprising at least one flap for joining the fastener assembly to an article.

11. The method of claim 10 in which the tab is formed by introducing a sheet material into a gap in which the base is molded, the sheet material being folded about a longitudinal fold line to form first and second overlapping fold portions and introduced under conditions selected to cause the second fold portion to become permanently bonded to resin of the base, while leaving the first fold portion free to be subsequently unfolded from said second fold portion about said fold line.

12. The method of claim 11 in which the sheet material is bonded to a surface of the base opposite the first surface from which the fastener elements extend.

13. The method of claim 11 in which the sheet material is bonded to said first surface of the base from which the fastener elements extend.

14. The method of claim 11 in which said second fold portion is bonded to the base only along a margin area of an exposed surface of said second fold portion.

15. The method of claim 14 in which unbonded surface areas of said first and second fold portions are protected from contact with the resin by a protective tape forming a barrier to the resin.

16. The method of claim 14 in which unbonded surface areas of said first and second fold portions are protected from contact with the resin by a protective coating forming a barrier to the resin.

17. The method of claim 1 further comprising forming dams along edges of the fastening section.

18. The method of claim 17 in which the dams are higher than said fastener elements.

19. The method of claim 1, wherein the fastener elements include head portions that extend from distal ends of the stem portions.

20. The method of claim 19, wherein the head portions are hook-shaped overhanging the sheet-form base in one or more discrete directions.

21. The method of claim 20, wherein the head portions are molded with the stem portions.

22. The method of claim 19, wherein the head portions are mushroom-shaped overhanging the sheet-form base in multiple directions.

23. A method of forming a fastening assembly comprising:
molding a continuous sheet-form base having a multiplicity of fastener elements having stem portions integrally molded with and extending from a fastening section of a surface of the base lying generally in a plane, the base, as molded, having a non-planar undulation in which the base extends out of its plane to form a peak that extends along a longitudinal direction of said base with opposite major surfaces of the base remaining generally parallel, the undulation being elastically deformable to enable said base to stretch laterally upon application of a lateral tensile force to the fastening assembly; and
coating the undulation with an elastomer.

24. The method of claim 23, wherein the fastener elements include head portions that extend from distal ends of the stem portions.

25. The method of claim 24, wherein the head portions are hook-shaped overhanging the sheet-form base in one or more discrete directions.

26. The method of claim 25, wherein the head portions are molded with the stem portions.

27. The method of claim 24, wherein the head portions are mushroom-shaped overhanging the sheet-form base in multiple directions.

28. The method of claim 24, wherein the elastomer is selected from the group consisting of thermoplastic elastomers, thermoplastic polyurethanes, elastomeric copolymers containing polyethylene terephthalate PET, thermoplastic olefins, and natural or synthetic rubber.

29. A method of forming a fastening assembly comprising:
molding a continuous sheet-form base having a multiplicity of fastener elements having stem portions integrally molded with and extending from a fastening section of a surface of the base lying generally in a plane, the base, as molded, has multiple, parallel non-planar undulations in which the base extends out of its plane to form peaks that extend along a longitudinal direction of said base with opposite major surfaces of the base remaining generally parallel, the undulations being elastically deformable to enable said base to stretch laterally upon application of a lateral tensile force to the fastening assembly; and
filling an area between adjacent peaks with an elastomer.

30. A method of forming a fastening assembly comprising:
molding a continuous sheet-form base having a multiplicity of fastener elements having stem portions integrally molded with and extending from a fastening section of a surface of the base lying generally in a plane, the base, as molded, having a non-planar undulation in which the base extends out of its plane to form a peak that extends along a longitudinal direction of said base with opposite major surfaces of the base remaining generally parallel, the undulation being elastically deformable to enable said base to stretch laterally upon application of a lateral tensile force to the fastening assembly; and
forming a tab joined with said base, the tab extending laterally from the undulation along a lateral margin of the fastener assembly opposite a second lateral margin more nearly adjacent the fastening section, the tab comprising at least one flap for joining the fastening assembly to an article;
wherein the tab is formed by introducing a sheet material into a gap in which the base is molded, the sheet material being folded about a longitudinal fold line to form first and second overlapping fold portions and introduced under conditions selected to cause the second fold portion to become permanently bonded to resin of the base, while leaving the first fold portion free to be subsequently unfolded from said second fold portion about said fold line.

31. The method of claim 30, wherein the sheet material is bonded to a surface of the base opposite the first surface from which the fastener elements extend.

32. The method of claim 30, wherein the sheet material is bonded to said first surface of the base from which the fastener elements extend.

33. The method of claim 30, wherein said second fold portion is bonded to the base only along a margin area of an exposed surface of said second fold portion.

34. The method of claim 33, wherein unbonded surface areas of said first and second fold portions are protected from contact with the resin by a protective tape forming a barrier to the resin.

35. The method of claim 33, wherein unbonded surface areas of said first and second fold portions are protected from contact with the resin by a protective coating forming a barrier to the resin.

36. A method of forming a fastening assembly comprising:

molding a continuous sheet-form base having a multiplicity of fastener elements having stem portions integrally molded with and extending from a fastening section of a surface of the base lying generally in a plane, the base, as molded, having a non-planar undulation in which the base extends out of its plane to form a peak that extends along a longitudinal direction of said base with opposite major surfaces of the base remaining generally parallel, the undulation being elastically deformable to enable said base to stretch laterally upon application of a lateral tensile force to the fastening assembly; and forming dams along edges of the fastening section.

37. The method of claim 36, wherein the dams are higher than the fastener elements.